US008344025B2

(12) United States Patent
Surburg et al.

(10) Patent No.: US 8,344,025 B2
(45) Date of Patent: Jan. 1, 2013

(54) OXALIC ACID DERIVATIVES AND USE THEREOF AS PHYSIOLOGICAL COOLING ACTIVE INGREDIENTS

(75) Inventors: Horst Surburg, Holzminden (DE); Jan Looft, Holzminden (DE); Heiko Oertling, Holzminden (DE); Tobias Vössing, Beverungen (DE)

(73) Assignee: Symrise AG, Holzminden (DE)

( * ) Notice: Subject to any disclaimer, the term of this patent is extended or adjusted under 35 U.S.C. 154(b) by 699 days.

(21) Appl. No.: 12/193,375

(22) Filed: Aug. 18, 2008

(65) Prior Publication Data

US 2009/0054520 A1    Feb. 26, 2009

Related U.S. Application Data

(60) Provisional application No. 60/956,726, filed on Aug. 20, 2007.

(51) Int. Cl.
 A61K 31/215    (2006.01)
 C07C 69/608    (2006.01)
 A61P 11/00    (2006.01)

(52) U.S. Cl. ...................................... 514/529; 560/127
(58) Field of Classification Search .................. 514/529; 560/127
See application file for complete search history.

(56) References Cited

U.S. PATENT DOCUMENTS

| | | | |
|---|---|---|---|
| 4,407,810 A | 10/1983 | Eilingsfeld et al. | |
| 4,518,615 A | 5/1985 | Cherukuri et al. | |
| 4,944,789 A * | 7/1990 | Rentzea et al. | 504/209 |
| 5,002,791 A | 3/1991 | Knebl | |
| 5,093,136 A | 3/1992 | Panhorst et al. | |
| 5,266,336 A | 11/1993 | McGrew et al. | |
| 5,458,894 A | 10/1995 | Knebl et al. | |
| 5,601,858 A | 2/1997 | Mansukhani et al. | |
| 5,725,865 A | 3/1998 | Mane et al. | |
| 5,843,466 A | 12/1998 | Mane et al. | |
| 6,326,014 B1 * | 12/2001 | Tuloup et al. | 424/401 |
| 6,432,441 B1 | 8/2002 | Bealin-Kelly et al. | |
| 6,986,709 B2 | 1/2006 | Hughs-Baird et al. | |
| 6,986,907 B2 | 1/2006 | Phillips et al. | |
| 2002/0188019 A1 | 12/2002 | Ley et al. | |
| 2004/0241312 A1 | 12/2004 | Gatfield et al. | |
| 2005/0191325 A1* | 9/2005 | Remon | 424/400 |
| 2005/0222256 A1 | 10/2005 | Erman et al. | |

FOREIGN PATENT DOCUMENTS

| | | |
|---|---|---|
| DE | 1002318 | 2/1957 |
| DE | 2413966 | 9/1974 |
| DE | 2608226 | 9/1977 |
| DE | 3027527 | 2/1982 |
| DE | 4226043 | 2/1994 |
| DE | 10351422 | 6/2005 |
| EP | 0242325 | 10/1987 |
| EP | 0350693 | 1/1990 |
| EP | 0507190 | 10/1992 |
| EP | 1493336 | 1/2005 |
| JP | 2004059474 | 2/2004 |
| JP | 2005343795 | 12/2005 |
| WO | WO-0170687 | 9/2001 |
| WO | WO-03092412 | 11/2003 |
| WO | WO-04000787 | 12/2003 |
| WO | WO-2004026840 | 4/2004 |
| WO | WO-2004050069 | 6/2004 |
| WO | WO-2004078302 | 9/2004 |
| WO | WO-2005096841 | 10/2005 |
| WO | WO-2006024587 | 3/2006 |
| WO | WO-2006058893 | 6/2006 |
| WO | WO-2006106023 | 10/2006 |
| WO | WO-2007003527 | 1/2007 |
| WO | WO-2007014879 | 2/2007 |

OTHER PUBLICATIONS

Dichloromethane Material Safety Data Sheet (MSDS) (2009).*
Qussi et al. Investigation of the effect of various shellac coating compositions containing different water-soluble polymers on in vitro drug release. Drug Dev. Ind. Pharm. 31, 99-108 (2005).*
Belokon' et al., "Enantioselective and diastereoselective syntheses of cyanohydrin carbonates", Tetrahedron, Elsevier Science Publishers, Amsterdam, NL, Bd. 63, Nr. 39, pp. 9724-9740, 2007.
Supplementary European Search Report, European Application No. EP08162309.2, received Jul. 15, 2009.
K.- F. Hebenbrock, et al., N-Substituierte Tetrahydro-1.3-oxazine und N-substituierete 1.3-Oxazolidine aus den entsprechenden N-Nitroso-Verbindungen **, Liebigs Ann. Chem. 765, 1972, pp. 78-93.
H.R. Watson, et al., New compounds with the menthol cooling effect, J. Soc. Cosmet. Chem., 29, 1978, pp. 185-200.

* cited by examiner

*Primary Examiner* — Barbara P Badio
*Assistant Examiner* — Sara E Townsley
(74) *Attorney, Agent, or Firm* — Connolly Bove Lodge & Hutz LLP

(57) ABSTRACT

The present invention relates to specific oxalic acid derivatives and to corresponding mixtures and to uses thereof as physiological cooling active ingredients.

25 Claims, No Drawings

OXALIC ACID DERIVATIVES AND USE THEREOF AS PHYSIOLOGICAL COOLING ACTIVE INGREDIENTS

CROSS-REFERENCE TO RELATED APPLICATION

This application claims benefit of priority to U.S. Provisional Application No. 60/956,726, filed on Aug. 20, 2007, which is incorporated herein by reference in its entirety.

The invention relates to specific oxalic acid derivatives and mixtures thereof which can bring about a physiological cooling action on the skin and/or a mucous membrane. It also relates to mixtures and preparations which contain the oxalic acid derivatives in a sufficient amount for a cooling action to be produced on the skin and/or mucous membranes. It moreover relates to the use of the stated compounds as a cooling substance or for the production of a medicament and to a method for achieving a physiological cooling action on the skin and/or mucous membranes.

Physiological cooling active ingredients are often used to bring about a sensation of coolness on the skin or mucous membranes, for example on the mucous membranes in the oral, nasal and/or pharyngeal cavities, but without any physical cooling, such as occurs for example on solvent evaporation, actually occurring. Both individual components and mixtures may be used as physiological cooling active ingredients.

The best known cooling active ingredient is L-menthol, but this exhibits various disadvantages, for example a strong odor impression, elevated volatility and, at relatively high concentrations, a bitter and/or spicy hot intrinsic taste. In certain aroma compositions, in particular those which do not tend towards a (pepper)mint aroma, the use of L-menthol may thus be undesirable.

Investigations have already been carried out which were directed towards strong cooling active ingredients without an aroma effect. Lactic acid esters of menthol(s) according to DE 2 608 226 and mixed carbonates with menthol(s) and polyols according to DE 4 226 043 and menthone ketals according to EP 0 507 190 have, for example, been described.

While menthyl monoesters of diacids according to U.S. Pat. No. 5,725,865 and U.S. Pat. No. 5,843,466 are indeed interesting naturally occurring alternatives, in sensory testing they cannot achieve the strength of previously described cooling active ingredients.

J. Soc. Cosmet. Chem. 1978, 29, 185-200 presented the results of a study of approx. 1200 compounds, in which the compounds L-menthane carboxylic acid N-ethylamide ("WS3"), and in particular $N^{\alpha}$-(L-menthanecarbonyl)glycine ethyl ester ("WS5") were found to be the most strongly cooling active ingredients. The latter, while having a strong action, has the disadvantage of being susceptible to hydrolysis and, as a result, forming the corresponding free acid $N^{\alpha}$-(L-menthanecarbonyl)glycine, which itself exhibits only a very weak cooling action. Despite the exhaustive investigations which have been described, a systematic prediction of the properties of potential cooling active ingredients, in particular regarding the bitterness thereof and/or the other trigeminal effects thereof, is not possible and has also not been described. Accordingly, while many molecules falling within the class of menthane carboxamides are indeed strongly cooling, they frequently simultaneously exhibit marked bitter notes (for example the menthane carboxylic acid N-(alkyloxyalkyl)amides according to JP 2004059474) or are additionally strongly irritant (WS5: N-[[5-methyl-2-(1-methylethyl)cyclohexyl]carbonyl]glycine ethyl ester, US 2005/0222256).

$N^{\alpha}$-(Menthanecarbonyl)alkyloxyalkylamides have been described in JP 2004059474. These have a strong cooling action and elevated resistance to hydrolysis, but suffer the disadvantage of being strongly bitter and thus being unusable in foodstuffs and also in cosmetic products for facial care.

Menthyl glyoxylates and the hydrates thereof have moreover been described as cooling substances in JP 2005343795.

EP 1 493 336 describes monomenthyl ester derivatives of succinic acid and the corresponding higher homologues as cooling substances. On tasting by an expert panel in direct comparison with compounds of the formula (I), it became clear that the described oxamates are organoleptically superior to the monomenthyl esters since, while exhibiting a comparable cooling action, they do not have a bitter, spicy hot accompanying taste.

The primary object of the present invention was to provide novel compounds or mixtures of compounds which have a strong physiological cooling action and may consequently be used as cooling substances (cooling active ingredients) in foodstuffs and/or products consumed for pleasure and/or oral care products and/or (oral) pharmaceutical preparations and/or cosmetic preparations. The compounds or mixtures of compounds to be provided should preferably exhibit the weakest possible intrinsic taste, in particular should taste only slightly or not at all bitter and exhibit the slightest possible irritancy.

This primary object is achieved according to the invention by (a) a compound of the formula (I) and by (b) a mixture comprising one, two or more compounds of the formula (I) and by (c) a mixture consisting of two or more compounds of the formula (I)

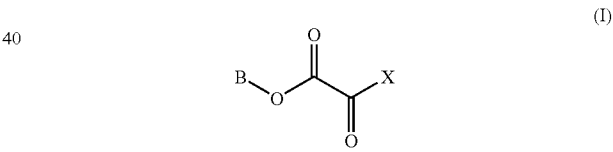

(I)

wherein the following in each case applies:

B means a hydrocarbon residue selected from the following group:

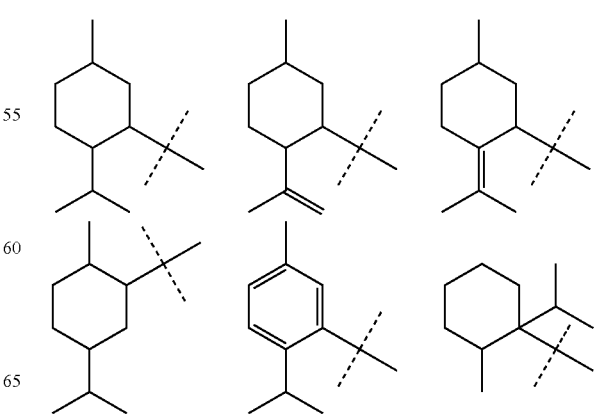

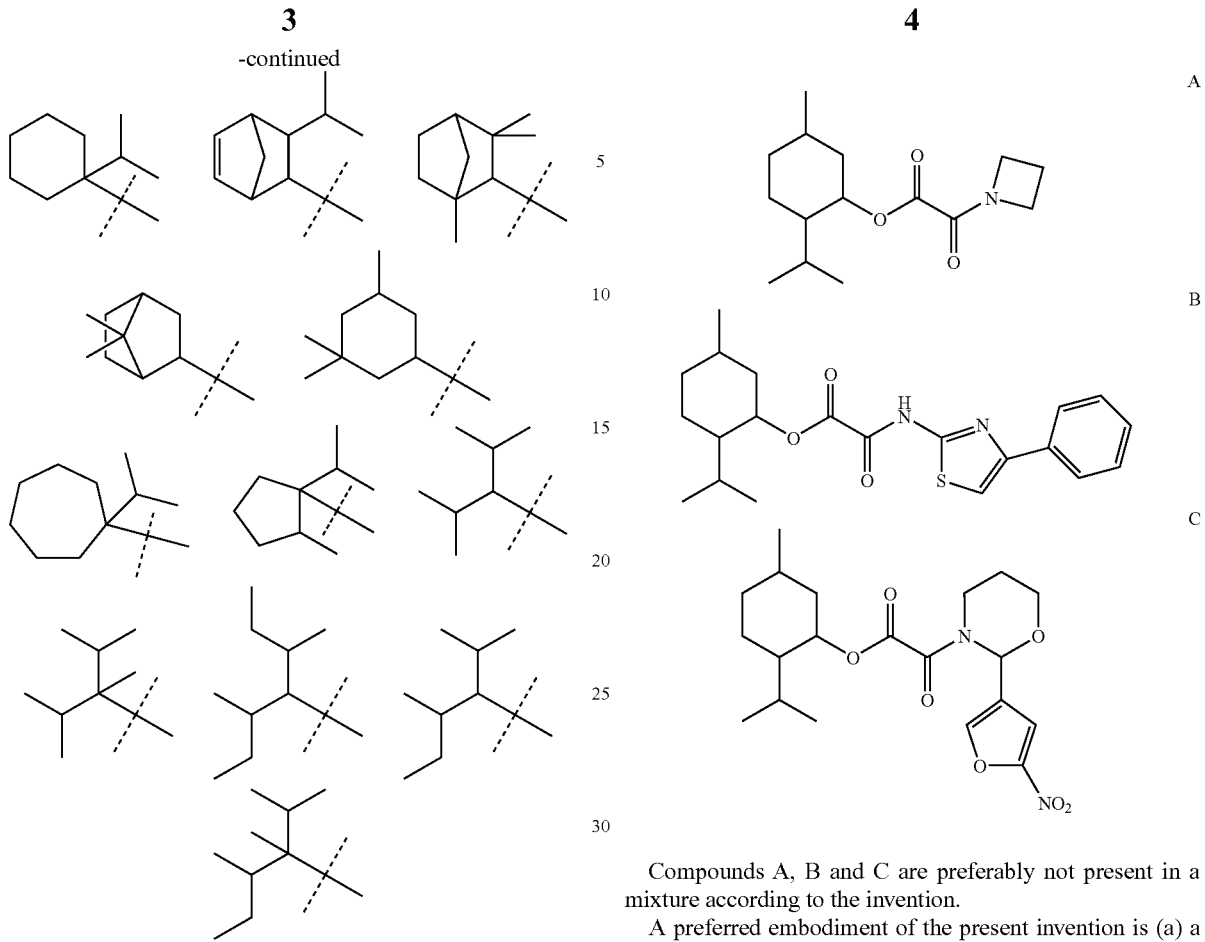

in which the dashed line indicates the bond which links the hydrocarbon residue B with the adjacent oxygen atom in formula (I).

X means $NR^1R^2$ or $SR^3$, wherein in each case mutually independently in $NR^1R^2$ the residues $R^1$ and $R^2$ are selected and in $SR^3$ the residue $R^3$ is selected from the group consisting of:

hydrogen and organic residue with 1 to 12 C atoms which is preferably selected from the group consisting of substituted or unsubstituted alkyl, heteroalkyl, cycloalkyl, heterocycloalkyl, cycloalkylalkyl, alkenyl, cycloalkenyl, cycloalkenylalkyl, alkynyl, cycloalkylalkynyl, aryl, heteroaryl, arylalkyl, cycloalkylaryl, cycloalkenylaryl, cycloalkylheteroaryl, heterocycloalkylaryl, heterocycloalkenylaryl, heterocycloalkenylheteroaryl and heteroarylalkyl, wherein optionally in $NR^1R^2$ the residues $R^1$ and $R^2$ are covalently bonded together with omission of one hydrogen atom in each case and with formation of a ring, providing that in the above-case (a) the compound of the formula (I) and in case (b) at least one compound of the formula (I) is not selected from the group consisting of:

Compounds A, B and C are preferably not present in a mixture according to the invention.

A preferred embodiment of the present invention is (a) a compound of the formula (I) or (b) a mixture comprising one, two or more compounds of the formula (I) or (c) a mixture consisting of two or more compounds of the formula (I) as described above, wherein in case (a) the compound or in case (b) or (c) at least one of the compounds in the mixture is selected from the group consisting of compounds of the formula (I), wherein the following applies:

X means $NR^1R^2$ or $SR^3$, wherein in each case mutually independently in $NR^1R^2$ the residues $R^1$ and $R^2$ are selected and in $SR^3$ the residue $R^3$ is selected from the group consisting of:

hydrogen and organic residue with 1 to 12 C atoms and optionally up to 3 heteroatoms, which are in each case mutually independently selected from the group consisting of N, S and O, wherein optionally present heteroatoms from the group consisting of O and S are not covalently bonded to other heteroatoms from this group, wherein a number of hydrogen atoms attached to C is optionally replaced by fluorine, wherein the organic residue in each case including all optionally present substituents contains no further heteroatoms from the group consisting of N, S and O as C atoms and is selected from the group consisting of substituted or unsubstituted $C_1$-$C_{10}$ alkyl, $C_1$-$C_{10}$ heteroalkyl, $C_2$-$C_{10}$ heterocycloalkyl, $C_3$-$C_{10}$ cycloalkyl, $C_4$-$C_{10}$ cycloalkylalkyl, $C_2$-$C_{10}$ alkenyl, $C_3$-$C_{10}$ cycloalkenyl, $C_4$-$C_{10}$ cycloalkenylalkyl, $C_2$-$C_{10}$ alkynyl, $C_5$-$C_{10}$ cycloalkylalkynyl, $C_3$-$C_{10}$ aryl, $C_2$-$C_{10}$ heteroaryl, $C_4$-$C_{10}$ arylalkyl, $C_8$-$C_{10}$ cycloalkylaryl, $C_8$-$C_{10}$ cycloalkenylaryl, $C_5$-$C_{10}$ cycloalkylheteroaryl, $C_8$-$C_{10}$ heterocycloalkylaryl, $C_8$-$C_{10}$ heterocycloalkenylaryl, $C_8$-$C_{10}$ heterocycloalkenylheteroaryl and $C_3$-$C_{10}$ heteroarylalkyl,
and is preferably selected from the group consisting of substituted or unsubstituted
$C_1$-$C_8$ alkyl, $C_2$-$C_8$ heteroalkyl, $C_1$-$C_8$ heterocycloalkyl, $C_3$-$C_8$ cycloalkyl; $C_4$-$C_8$ cycloalkylalkyl, $C_2$-$C_8$ alkenyl, $C_3$-$C_8$ cycloalkenyl, $C_4$-$C_8$ cycloalkenylalkyl, $C_3$-$C_6$ aryl, $C_2$-$C_6$ heteroaryl, $C_4$-$C_8$ arylalkyl,
wherein optionally in $NR^1R^2$ the residues $R^1$ and $R^2$ are covalently bonded together with omission of one hydrogen atom in each case and with formation of a ring.

In case (b) or (c) each compound of the formula (I) present in the mixture is preferably selected from said group.

A particularly preferred embodiment of the present invention is (a) a compound of the formula (I) or (b) a mixture comprising one, two or more compounds of the formula (I) or (c) a mixture consisting of two or more compounds of the formula (I) according to one of the above-described embodiments, wherein in case (a) the compound or in case (b) or (c) at least one of the compounds in the mixture is selected from the group consisting of compounds of the formula (I), wherein the following applies
X means $NR^1R^2$,
wherein in each case mutually independently
in $NR^1R^2$ the residues $R^1$ and $R^2$ are selected from the group consisting of:
hydrogen
and
organic residue with
1 to 12 C atoms and
optionally up to 3 heteroatoms, which are in each case mutually independently selected from the group consisting, of N, S and O, wherein optionally present heteroatoms from the group consisting of O and S are not covalently bonded to other heteroatoms from this group,
wherein a number of hydrogen atoms attached to C is optionally replaced by fluorine,
wherein the organic residue in each case including all optionally present substituents contains no further heteroatoms from the group consisting of N, S and O as C atoms and is selected from the group consisting of substituted or unsubstituted
$C_1$-$C_4$ alkyl, $C_2$-$C_5$ heteroalkyl, $C_3$-$C_6$ cycloalkyl, $C_3$-$C_6$ aryl, $C_2$-$C_6$ heteroaryl, $C_4$-$C_8$ arylalkyl
and is preferably selected from the group consisting of
methyl, ethyl, n-propyl, n-butyl, iso-butyl, sec.-butyl, tert.-butyl, 2-hydroxyethyl, 3-hydroxypropyl, methoxymethyl, 2-methoxyethyl, 3-methoxypropyl, 2-ethoxyethyl, 3-ethoxypropyl, cyclopropyl, 2,2-dimethylcyclopropyl, cyclopentyl, cyclohexyl, phenyl, p-toluyl, p-anisyl, 2-furfuryl, 2-pyrrolidyl, 2-pyridinyl, and benzyl,
wherein in $NR^1R^2$ the residues $R^1$ and $R^2$ are covalently bonded together with omission of one hydrogen atom in each case and with formation of a ring.

The most marked cooling action was exhibited by compounds according to the invention in which X means an $NHR^2$ group, and a preferred embodiment of the present invention is accordingly (a) a compound of the formula (I) or (b) a mixture comprising one, two or more compounds of the formula (I) or (c) a mixture consisting of two or more compounds of the formula (I) according to any one of the preceding claims, wherein in case (a) the compound or in case (b) or (c) at least one of the compounds in the mixture is selected from the group consisting of compounds of the formula (I), wherein the following applies:
X means $NHR^1$
wherein $R^1$ has the above-stated meaning.

In case (b) or (c) each compound of the formula (I) present in the mixture is preferably selected from said group.

An embodiment of the present invention preferred because of its excellent cooling action is (a) a compound of the formula (I) or (b) a mixture comprising one, two or more compounds of the formula (I) or (c) a mixture consisting of two or more compounds of the formula (I) according to one of the above-described embodiments, wherein in case (a) the compound or in case (b) or (c) at least one of the compounds in the mixture is selected from the group consisting of compounds of the formula (I), wherein the following applies:
B means a hydrocarbon residue selected from the group consisting of:

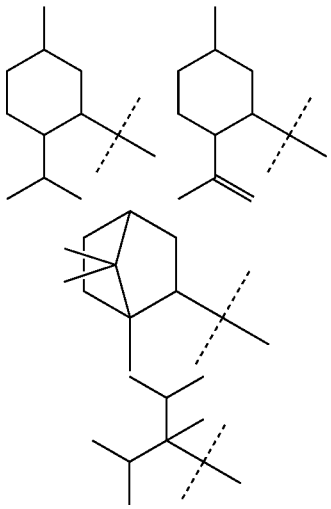

wherein it is particularly preferred for B to mean a hydrocarbon residue selected from the following group:
L-menthyl, D-menthyl or rac-menthyl.

In case (b) or (c) each compound of the formula (I) present in the mixture is preferably selected from said group.

A further preferred embodiment of the present invention is (a) a compound of the formula (I) or (b) a mixture comprising one, two or more compounds of the formula (I) or (c) a mixture consisting of two or more compounds of the formula (I) according to one of the above-described embodiments, wherein in case (a) the compound or in case (b) or (c) at least one of the compounds in the mixture is selected from the group consisting of compounds of the formula (I), wherein individual but preferably all optionally present substituents of the optionally present residues $R^1$, $R^2$ and $R^3$ are mutually independently selected from the group consisting of:
$C_1$-$C_5$ alkyl, $C_3$-$C_8$ cycloalkyl, $C_2$-$C_4$ alkenyl, $C_2$-$C_4$ alkynyl, propynyl, $C_1$-$C_4$ perfluoroalkyl, hydroxy, $C_1$-$C_8$ alkoxy, $C_3$-$C_8$ cycloalkoxy, $C_1$-$C_4$ acyl, $C_1$-$C_4$ alkoxycarbonyl, $C_1$-$C_4$ acyloxy or $C_2$-$C_7$ heteroalkyl
and are preferably selected from the group consisting of:
methyl, ethyl, n-propyl, iso-propyl, n-butyl, iso-butyl, tert.-butyl, cyclopropyl, cyclopentyl, cyclohexyl, cyclooctyl, ethenyl, propenyl, ethynyl, propynyl, trifluoromethyl, methoxy, ethoxy, iso-propoxy, n-butoxy, iso-butoxy, tert.-butoxy, $C_3$ cycloalkoxy, $C_5$ cycloalkoxy, $C_6$ cycloalkoxy, $C_8$ cycloalkoxy, —[—O—$CH_2$—$CH_2$—]$_v$-Q or —[—O—$CH_2$—CHMe—]$_v$-Q, wherein Q=OH or is $CH_3$ and wherein v may mean 1 or 2, acetyl, $CO_2$Me, $CO_2$Et, $CO_2$iso-Pr, $CO_2$tert.-Bu, acetyloxy.

In case (b) or (c) each compound of the formula (I) present in the mixture is preferably selected from said group.

A further preferred embodiment of the present invention is (a) a compound of the formula (I) or (b) a mixture comprising one, two or more compounds of the formula (I) or (c) a mixture consisting of two or more compounds of the formula (I) according to one of the above-described embodiments, wherein in case (a) the compound or in case (b) or (c) at least one of the compounds in the mixture is selected from the group consisting of compounds of the formula (I), wherein the residues $R^1$ and $R^2$ of the group $NR^1R^2$ are covalently bonded together with omission of in each case one hydrogen-atom and form an at most 7-membered ring, and preferably form a group $NR^1R^2$ which is selected from the group of the 6 or 7-membered rings and is particularly preferably selected from the group consisting of piperidinyl and morpholinyl.

Less preferable is the selection of four-membered rings, in particular if they are unsubstituted, and 5-membered rings, in particular if they contain (i) precisely one nitrogen atom and precisely one oxygen atom or (ii) precisely one nitrogen atom and precisely one sulfur atom in the ring.

A favorable combination of good physiological cooling action, weak intrinsic taste and low irritation is displayed by (a) a compound of the formula (I) or (b) a mixture comprising one, two or more compounds of the formula (I) or (c) a mixture consisting of two or more compounds of the formula (I) according to one of the above-described embodiments, wherein in case (a) the compound or in case (b) or (c) at least one of the compounds in the mixture is selected from the group consisting of compounds of the formula (I), wherein the following applies:

B means a hydrocarbon residue selected from the group consisting of:
L-menthyl, D-menthyl or rac-menthyl
X means $NR^1R^2$
wherein in each case mutually independently
the residues $R^1$ and $R^2$ are selected from the group consisting of:
hydrogen
and
organic residue with
1 to 12 C atoms and
optionally up to 3 heteroatoms, which are in each case mutually independently selected from the group consisting of N, S and O, wherein optionally present heteroatoms from the group consisting of O and S are not covalently bonded to other heteroatoms from this group,
wherein a number of hydrogen atoms attached to C is optionally replaced by fluorine,
wherein the organic residue in each case including all optionally present substituents contains no further heteroatoms from the group consisting of N, S and O as C atoms and is selected from the group consisting of substituted or unsubstituted
$C_1$-$C_4$ alkyl, $C_2$-$C_5$ heteroalkyl, $C_3$-$C_6$ cycloalkyl, $C_3$-$C_6$ aryl, $C_2$-$C_6$ heteroaryl, $C_4$-$C_8$ arylalkyl
wherein in $NR^1R^2$ the residues $R^1$ and $R^2$ are also optionally covalently bonded together with omission of one hydrogen atom in each case, wherein the resultant ring is at most 7-membered,
wherein the optionally present substituents of the optionally present residues $R^1$, $R^2$ and $R^3$ may mutually independently be selected from the group consisting of:
methyl, ethyl, n-propyl, iso-propyl, n-butyl, iso-butyl, tert.-butyl, cyclopropyl, cyclopentyl, cyclohexyl, cyclooctyl, ethenyl, propenyl, ethynyl, propynyl, trifluoromethyl, methoxy, ethoxy, iso-propoxy, n-butoxy, iso-butoxy, tert.-butoxy, $C_3$ cycloalkoxy, $C_5$ cycloalkoxy, $C_6$ cycloalkoxy, $C_5$ cycloalkoxy, —[—O—$CH_2$—$CH_2$—]$_v$-Q or —[—O—$CH_2$—CHMe—]$_v$-Q, wherein Q=OH or is $CH_3$ and wherein v may mean 1 or 2, acetyl, $CO_2Me$, $CO_2Et$, $CO_2iso$-Pr, $CO_2tert$.-Bu, acetyloxy.

A particularly favorable combination of good physiological cooling action, a tendency towards a weak intrinsic taste and low irritation is displayed by (a) a compound of the formula (I) or (b) a mixture comprising one, two or more compounds of the formula (I) or (c) a mixture consisting of two or more compounds of the formula (I) according to one of the above-described embodiments, wherein in case (a) the compound or in case (b) or (c) at least one of the compounds in the mixture is selected from the group consisting of menthyl oxamate menthyl N-methyl oxamate menthyl N,N-dimethyl oxamate menthyl N-ethyl oxamate menthyl N,N-diethyl oxamate menthyl N-propyl oxamate menthyl N,N-dipropyl oxamate menthyl N-isopropyl oxamate menthyl N,N-diisopropyl oxamate menthyl N-cyclopropyl oxamate menthyl N-butyl oxamate morpholinyl-oxo-acetic acid (1R,2S,5R)-2-isopropyl-5-methylcyclohexyl ester menthyl N-(2-methoxyethyl)oxamate menthyl N-(3-methoxypropanol)oxamate menthyl N-(2-hydroxyethyl)oxamate menthyl N-(3-hydroxypropyl)oxamate.

In case (b) or (c) each compound of the formula (I) present in the mixture is preferably selected from said group.

Likewise particularly preferred is (a) a compound of the formula (I) or (b) a mixture comprising one, two or more compounds of the formula (I) or (c) a mixture consisting of two or more compounds of the formula (I) according to one of the above-described embodiments, wherein in case (a) the compound or in case (b) or (c) at least one of the compounds: in the mixture is selected from the group consisting of L-menthyl N-methyl oxamate, D-menthyl N-methyl oxamate, rac-menthyl N-methyl oxamate, L-menthyl N-ethyl oxamate, D-menthyl N-ethyl oxamate, rac-menthyl N-ethyl oxamate.

In case (b) or (c) each compound of the formula (I) present in the mixture is preferably selected from said group.

L-Menthyl oxamates are most preferred, since they provide the best solution to the problem underlying this invention.

Individual compounds of the formula (I) and the synthesis thereof have been described in the literature, but not a physiological cooling action or corresponding uses or methods. For an example of synthesis of oxamates, reference is made to DE 1 002 318 and DE 2 413 966.

The following compounds A, B and C, which come under the above-defined formula (I), have already been described, specifically A in EP 0 350 693, compound B in DE 3027 527 A1 and U.S. Pat. No. 4,407,810 and compound C in Liebigs Ann. Chem. 765, 1972, 78. A compound D, which is structurally still distantly related, is described in WO 0117068.

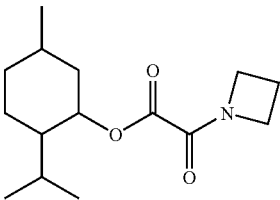

A

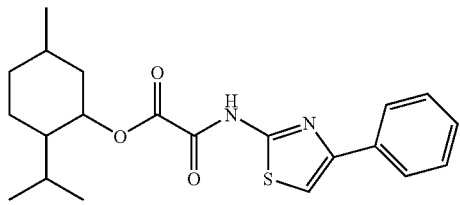

B

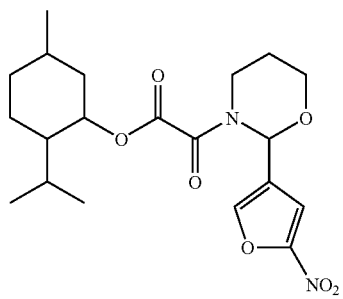

C

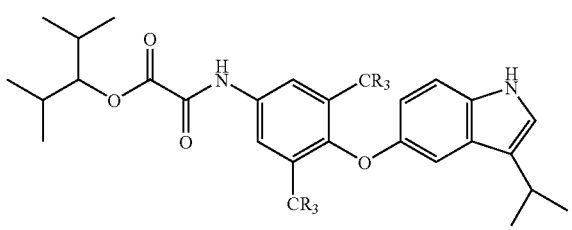

D

R = H or F

Compounds which are likewise still structurally related are described in the published patent application DE 2 413 966, which describes oxamic acid derivatives of the formula $ANHCOCO_2R^5$ in which $R^5$ means a group such as lower alkyl, cycloalkyl, aralkyl etc. and in particular also cyclohexyl and the residues A are pyridyl, pyrazinyl, pyrimidyl or phenyl.

Compounds A, B and C are not as such provided by the present invention, and nor are mixtures which comprise just one of the compounds A, B or C but no further compounds of the formula (I) with the above-stated meanings of B and X. All in all, the compounds of the formula (I) disclosed in EP 0 350 693, DE 3027 527 A1, U.S. Pat. No. 4,407,810, Liebigs Ann. Chem. 765, 1972, 78 and the still structurally related compounds disclosed in DE 2 413 966 and WO 01/70687 (the mixtures disclosed therein which comprise these compounds and the production methods disclosed therein for these compounds) are not provided by the present invention or not preferred for the purposes of the present invention. In particular, compounds in which —$NR^1R^2$ means substituted or unsubstituted azetidine or $NHR^1$, wherein $R^1$ is substituted 2-thiazolyl, are not preferred. Oxamic acid derivatives of the formula $ANHCOCO_2R^5$ according to DE 2 413 966 with $R^5$=cyclohexyl are no more provided by the present invention than the corresponding compounds in which $R^5$ is unsubstituted cycloalkyl, with the same applying to mixtures which merely comprise such compounds, but no compounds of the formula (I) with the above-stated meanings of B and X according to the invention.

The invention is based on the surprising recognition that the compounds according to the invention, oxalic acid derivatives of the formulae (I) and mixtures thereof, cause a strong and long-lasting sensation of coldness on the skin or mucous membrane, in particular on the mucous membranes of the oral, nasal and pharyngeal cavities. Said compounds here exhibit no other trigeminal effects such as spiciness, tingling or numbing and are not bitter. At the same time, within the bounds of conventional formulations and conditions of preparation, the compounds according to the invention are resistant to hydrolysis in the range from pH 1 to pH 12, in particular in the range from pH 4 to pH 9, in relation to preparations containing water, such that the compounds and mixtures according to the invention have a long storage life in preparations and the particular preparation itself in turn has a long storage life.

The invention also relates to a mixture (b) as described above, consisting of or comprising
(1) one, two or more compounds of the formula (I)
and
(2) one or more further substances (i.e. not covered by the formula (I)) having a physiological cooling action, wherein the further substance or one, several or all of the further substances (i) cause(s) a taste-effect or (ii) cause(s) no taste effect,
and/or
(3) one or more aroma substances without a physiological cooling action
and/or
(4) one or more substances without a physiological cooling action which have a trigeminal or salivatory action.

A particularly preferred mixture according to the invention is one comprising as constituent (2) one or more further substances with a physiological cooling action, these causing no taste effect and no aroma action, but instead merely a cooling action (substantially) without any further organoleptic effect. This prevents the aroma profile of the mixture according to the invention being for example shifted towards "mint" (peppermint).

A very particularly preferred mixture according to the invention is one comprising as constituent (3) one or more aroma substances without a physiological cooling action and/or as constituent (4) one or more compounds which mutually independently or jointly additionally cause a taste-modulating effect and/or a trigeminal and/or a salivatory stimulus, wherein the trigeminal stimulus preferably does not constitute a physiological cooling action. In particular, such mixtures according to the invention which simultaneously contain the latter-stated constituents (3) and (4) have a pleasant cooling action and a balanced organoleptic profile with a simultaneously elevated impact, i.e. an elevated initial taste impression.

The one or more further substances with physiological cooling action which may be used as constituent (2) in a mixture according to the invention are preferably selected from the following list: menthol and menthol derivatives (for example L-menthol, D-menthol, racemic menthol, isomenthol, neoisomenthol, neomenthol), menthyl ethers (for example (L-menthoxy)-1,2-propanediol, (L-menthoxy)-2-methyl-1,2-propanediol, L-menthyl methyl ether), menthyl esters (for example menthyl formate, menthyl acetate, menthyl isobutyrate, menthyl lactate, L-menthyl L-lactate, L-menthyl D-lactate, menthyl(2-methoxy)acetate, menthyl (2-methoxyethoxy)acetate, menthyl pyroglutamate), menthyl carbonates (for example menthyl propylene glycol carbonate, menthyl ethylene glycol carbonate, menthyl glycerol carbonate or mixtures thereof), the semi-esters of menthol with a dicarboxylic acid or the derivatives thereof (for example monomenthyl succinate, monomenthyl glutarate, monomenthyl malonate, O-menthyl succinate N,N-(dimethyl)amide, O-menthyl succinamide), menthane carboxamides (here preferably menthane carboxylic acid N-ethylamide [WS3], N$^\alpha$-(menthane carbonyl)glycine ethyl ester [WS5], or menthane carboxylic acid N-(4-methoxyphenyl)amide [WS12], as described in U.S. Pat. No. 4,150,052, menthane carboxylic acid N-(4-cyanophenyl)amide, or menthane carboxylic acid N-(4-cyanomethylphenyl)amide as described in WO 2005/049553, menthane carboxylic acid N-(alkoxyalkyl)amides), menthone and menthone derivatives (for example L-menthone glycerol ketal), 2,3-dimethyl-2-(2-propyl)-butanoic acid derivatives (for example 2,3-dimethyl-2-(2-propyl)-butanoic acid N-methylamide [WS23]) isopulegol and its esters (L-(−)-isopulegol, L-(−)-isopulegol acetate), menthane derivatives (for example p-menthane-3,8-diol), cubebol or synthetic or natural mixtures containing cubebol, pyrrolidone derivatives of cycloalkyldione derivatives (for example 3-methyl-2(1-pyrrolidinyl)-2-cyclopenten-1-one) or tetrahydropyrimidin-2-ones (for example icilin or related compounds, as described in WO 2004/026840).

The one or more further substances with a physiological cooling action which may be used as constituent (2) of a mixture according to the invention are particularly preferably substances which at least substantially cause a physiological cooling action without simultaneously causing a taste action. Such preferred substances are: menthyl ethers (for example (L-menthoxy)-1,2-propanediol, (L-menthoxy)-2-methyl-1,2-propanediol), more highly polar menthyl esters (for example menthyl lactates, L-menthyl L-lactate, L-menthyl D-lactate, menthyl (2-methoxy)acetate, menthyl(2-methoxyethoxy)acetate, menthyl pyroglutamate), menthyl carbonates (for example menthyl propylene glycol carbonate, menthyl ethylene glycol carbonate, menthyl glycerol carbonate), the semi-esters of menthol with a dicarboxylic acid or the derivatives thereof (for example monomenthyl succinate, monomenthyl glutarate, monomenthyl malonate, O-menthyl succinate N,N-(dimethyl)amide, O-menthyl succinamide), menthane carboxamides not according to the invention (for example menthane carboxylic acid N-ethylamide [WS3], N$^\alpha$-(menthane carbonyl)glycine ethyl ester [WS5], menthane carboxylic acid N-(4-cyanophenyl)amide, menthane carboxylic acid N-(alkoxyalkyl)amides), menthone derivatives (for example L-menthone glycerol ketal), 2,3-dimethyl-2-(2-propyl)-butanoic acid derivatives (for example 2,3-dimethyl-2-(2-propyl)-butanoic acid N-methylamide), pyrrolidone derivatives of cycloalkyldione derivatives (for example 3-methyl-2(1-pyrrolidinyl)-2-cyclopenten-1-one) or tetrahydropyrimidin-2-ones (for example icilin or related compounds, which are described in WO 2004/026840).

Both complex natural raw materials such as extracts obtained from plants and essential oils, or fractions and uniform substances obtained therefrom, and uniform synthetic or biotechnologically obtained aroma substances are suitable as aroma substances.

Examples of natural raw materials are:
peppermint oils, spearmint oils, *Mentha arvensis* oils, anise oils, clove oils, citrus oils, cinnamon oils, wintergreen oils, cassia oils, davana oils, pine-needle oils, eucalyptus oils, fennel oils, galbanum oils, ginger oils, camomile oils, caraway oils, rose oils, geranium oils, sage oils, yarrow oils, star anise oils, thyme oils, juniper berry oils, rosemary oils, angelica root oils, and fractions of these oils.

Examples of uniform aroma substances are:
anethole, menthol, menthone, isomenthone, menthyl acetate, menthofuran, menthyl methyl ether; mint lactone, eucalyptol, limonene, eugenol, pinene, sabinene hydrate, 3-octanol, carvone, gamma-octalactone, gamma-nonalactone, germacrene D, viridiflorol, 1,3E,5Z-undecatriene, isopulegol, piperitone, 2-butanone, ethyl formate, 3-octyl acetate, isoamyl isovalerate, hexanol, hexanal, cis-3-hexenol, linalool, alpha-terpineol, cis and trans carvyl acetate, p-cymol, thymol, 4,8-dimethyl-3,7-nonadien-2-one, damascenone, damascone, rose oxide, dimethyl sulfide, fenchol, acetaldehyde diethyl acetal, cis-4-heptenal, isobutyraldehyde, isovaleraldehyde, cis-jasmone, anisaldehyde, methyl salicylate, myrtenyl acetate, 8-ocimenyl acetate, 2-phenylethyl alcohol, 2-phenylethyl isobutyrate, 2-phenylethyl isovalerate, cinnamaldehyde, geraniol, nerol. In the case of chiral compounds, the stated aroma substances may be present as a racemate, as an individual enantiomer or as enantiomer-enriched mixtures.

Examples of further flavorings which may advantageously be combined with the compounds according to the invention of the formula (I) are for example substances with a physiological cooling action, i.e. substances which bring about a sensation of coldness on the skin or mucous membrane. Such cooling active ingredients are for example L-menthol, L-isopulegol, menthone acetals (for example menthone glycerol acetal), menthyl esters, esters prepared from menthol and hydroxycarboxylic acids with 2 to 6 C atoms (for example menthyl lactate), substituted menthane 3-carboxamides (for example menthane 3-carboxylic acid N-ethylamide), branched alkanecarboxamides (for example 2-isopropyl-N,2,3-trimethylbutanamide), 3,3,5-trimethylcyclohexanol, 3-menthoxy-1,2-propanediol, 3-menthoxy-2-methyl-1,2-propanediol, 2-menthoxyethanol, 2-menthoxypropanol, 3-menthoxypropanol, 4-menthoxybutanol, 2-hydroxyethyl menthyl carbonate, 2-hydroxypropyl menthyl carbonate, glycerol menthyl carbonate, N-acetyl glycine menthyl ester, menthylhydroxycarboxylic acid esters (for example menthyl 3-hydroxybutyrate), menthane-3,8-diol, menthyl 2-methoxyacetate, menthyl 2-(2-methoxyethoxy)acetate, menthyl monosuccinate, 2-mercaptocyclodecanone, menthyl 2-pyrrolidin-5-one carboxylate. Preferred substances with a physiological cooling action are menthyl esters, menthone acetals, menthane 3-carboxamides and branched alkanecarboxamides.

It is also advantageous to use the compounds according to the invention of the formula (I) in conjunction with substances which bring about a spicy hot taste or a sensation of hotness or heat on the skin and mucous membranes or prickling or tingling sensation in the oral cavity and pharynx, such as for examples paprika powder, chili pepper powder, paprika extracts, pepper extracts, chili pepper extracts, ginger root extracts, extracts from grains of paradise (*Aframomum melegueta*), paracress extracts (jambu oleoresin; *Spilanthes acmella*, or *Spilanthes oleracea*), Japanese pepper extracts (*Zanthoxylum piperitum*), *Kaempferia galanga* extracts, *Alpinia galanga* extracts, water pepper extracts (*Polygonium hydropiper*), capsaicin, dihdrocapsaicin, gingerol, paradol, shogaol, piperine, sanshool I, sanshool II, sanshoamide, spilanthol, carboxylic acid N-vanillylamides, in particular nonanbic acid N-vanillylamide, 2-nonenoic acid amides, in particular 2-nonenodic acid N-isobutylamide, 2-nonenoic acid N-4-hydroxy-3-methoxyphenylamide, alkyl ethers of 4-hydroxy-3-methoxybenzyl alcohol, in particular 4-hydroxy-3-methoxybenzyl n-butyl ether, alkyl ethers of 3-hydroxy-4-methoxybenzyl alcohol, alkyl ethers of 3,4-dimethoxybenzyl alcohol, alkyl ethers of 3-ethoxy-4-hydroxybenzyl alcohol, alkyl ethers of 3,4-methylenedioxybenzyl alcohol, acetals of vanillin, acetals of ethylvanillin, acetals of isovanillin, (4-hydroxy-3-methoxyphenyl)acetamides, in particular (4-hydroxy-3-methoxyphenyl)acetic acid N-n-octylamide, allyl isothiocyanate, nicotinaldehyde, methyl nicotinate, propyl nicotinate, 2-butoxyethyl nicotinate, benzyl nicotinate, 1-acetoxychavicol.

Preferred aroma substances without a physiological cooling action are those aroma substances which, in addition to their actual odorous aroma value, also cause a taste impression, a taste-modulating effect or a trigeminal, but non-cooling or also a salivatory stimulus. Preferred taste impressions are sweet, umami, bitter, salty and sour, preferred taste-modulating effects are bitter-masking, umami-enhancing, sweet-enhancing, salt-enhancing and sour-masking effects; preferred trigeminal stimuli are spiciness, heat, tingling and pungency.

Preferred modulating aroma substances and/or flavorings are preferably selected from the group consisting of adenosine 5'-monophosphate, cytidine 5'-monophosphate, inosine 5'-monophosphate, and the pharmaceutically acceptable salts thereof; lactisoles; 2,4-dihydroxybenzoic acid; 3-hydroxybenzoic acid; sodium salts, preferably sodium chloride, sodium lactate, sodium citrate, sodium acetate, sodium gluconate; hydroxyflavanones, such as for example eriodictyol, homoeriodictyol, and the sodium salts thereof; hydroxybenzoic acid amides, such as for example 2,4-dihydroxybenzoic acid vanillylamide, 2,4-dihydroxybenzoic acid N-(4-hydroxy-3-methoxybenzyl)amide, 2,4,6-trihydroxybenzoic acid N-(4-hydroxy-3-methoxybenzyl)amide, 2-hydroxybenzoic acid: N-(4-hydroxy-3-methoxybenzyl)amide, 4-hydroxybenzoic acid N-(4-hydroxy-3-methoxybenzyl)amide, 2,4-dihydroxybenzoic acid N-(4-hydroxy-3-methoxybenzyl) amide monosodium salt, 2,4-dihydroxybenzoic acid N-2-(4-hydroxy-3-methoxyphenyl)ethylamide, 2,4-dihydroxybenzoic acid N-(4-hydroxy-3-ethoxybenzyl)amide, 2,4-dihydroxybenzoic acid. N-(3,4-dihydroxybenzyl)amide and 2-hydroxy-5-methoxy-N-[2-(4-hydroxy-3-methoxyphenyl) ethyl]amide; 4-hydroxybenzoic acid vanillylamide (in particular as described in WO 2006/024587, which is incorporated into this application by way of reference with regard to the corresponding compounds disclosed therein); hydroxydeoxybenzoins, such as for example 2-(4-hydroxy-3-methoxyphenyl)-1-(2,4,6-trihydroxyphenyl)ethanone, 1-(2,4-dihydroxyphenyl)-2-(4-hydroxy-3-methoxyphenyl)ethanone, 1-(2-hydroxy-4-methoxyphenyl)-2-(4-hydroxy-3-methoxyphenyl)ethanone) (in particular those as described in WO 2006/106023, which is incorporated into this application by way of reference with regard to the corresponding compounds disclosed therein); hydroxyphenylalkadiones, such as for example gingerdione-[2], gingerdione-[3], gingerdione-[4], dehydrogingerdione-[2], dehydrogingerdione-[3], dehydrogingerdione-[4]) (in particular those as described in WO 2007/003527, which is incorporated into this application by way of reference with regard to the corresponding compounds disclosed therein); diacetyl trimers (in particular those as described in WO 2006/058893, which is incorporated into this application by way of reference with regard to the corresponding compounds disclosed therein); γ-aminobutyric acid as described in WO 2005/096841, which is incorporated into this application by way of reference with regard to the corresponding compounds disclosed therein), divanillin as described in WO 2004/078302 and hesperetin according to WO 2007/014879.

Likewise particularly preferred aroma substances without a physiological cooling action are salivatory substances such as pellitorines according to WO 04/000787 or US 2004/0241312 and alkamides according to DE 103 51 422.

The invention also relates to corresponding methods for producing compounds according to the invention or for producing mixtures of compounds according to the invention.

Synthesis of the compounds according to the invention of the formula (E) (compound of the formula (I) with $X=NR^1R^2$) or synthesis of corresponding mixtures is preferably achieved by reacting the corresponding alcohol B—OH (wherein B has the above-stated meaning) with (a) oxalyl chloride and then with a corresponding amine $HNR^1R^2$ or (b) dialkyl oxalate and then with a corresponding amine $HNR^1R^2$ or (c) alkyl chlorooxoacetate and then with a corresponding amine $HNR^1R^2$ or (d) the corresponding aminooxoacetyl chloride.

Synthesis of the compounds according to the invention of the formula (i) with $X=SR^3$ proceeds similarly.

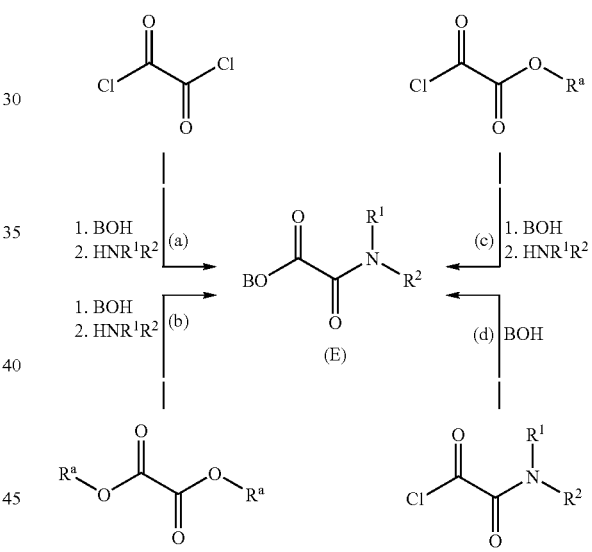

In this respect, the residues $R^a$ in each case mutually independently mean an alkyl residue, preferably a $C_1$-$C_4$ alkyl residue, preferably methyl or ethyl.

A further method for producing a compound according to the invention according to formula (I) comprises the steps:

(1) providing a mixed oxalic acid ester of the formula

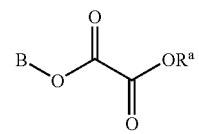

wherein $R^a$ means an alkyl residue, preferably $C_1$-$C_4$ residue, preferably methyl or ethyl, and B has the above-stated meaning, or an oxalic acid halide, preferably oxalic acid chloride, of the formula

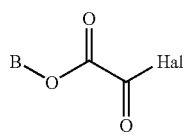

wherein Hal means halide, preferably Cl or Br, particularly preferably Cl, and wherein B has the above-stated meaning,
(2) providing an amine $HNR^1R^2$ or thiol $HSR^3$ or a corresponding salt, wherein $R^1$, $R^2$ and $R^3$ have the above-stated meanings,
(3) reacting the provided compounds with one another, resulting in a compound according to the invention.

A particularly preferred synthetic pathway may be illustrated by means of the following reaction scheme, which leads to a compound of the formula (Ia), wherein $R^1$ and $R^2$ in each case have the above-stated meanings. A corresponding synthetic pathway is preferred for the production of a compound of the formula (Ia).

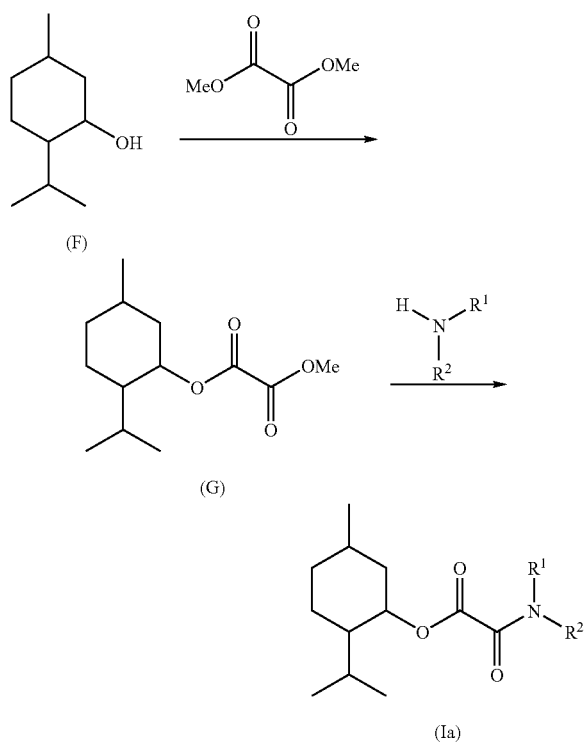

In this respect, the alcohol, here menthol (F), may be converted for example using known methods by means of dimethyl oxalate and a catalyst into the corresponding mixed oxalate (G).

This reaction may optionally proceed in the presence of other (auxiliary) substances or additives, for example in the presence of
(i) one or more solvents or diluents (for example toluene, 1,4-dioxane, dichloromethane, tetrahydrofuran, other ethers, chloroform, ethyl acetate, acetone, alkanes, cycloalkanes, alcohols)
and/or
(iii) phase-transfer catalysts (for example peralkylated/perarylated ammonium salts or phosphonium salts, crown ethers).

The crude synthesis products are preferably purified or concentrated by physical, optionally also enantioselective or enantiospecific separation methods, for example extraction, partition methods, crystallization, distillation, chromatography, sublimation, steam distillation, reverse osmosis, permeation or the like, the separation method preferably being selected such that, after the separation operation, the stereochemistry of the compounds according to the invention of the formula (I) (to the extent that the formula (I) defines the stereochemistry) corresponds to a proportion of 90-100 mol %, preferably 95-100 mol %, relative to the total amount of the compounds of the formula (I) present in the purified product.

The invention also relates to preparations serving for nutrition or for pleasure or used for oral hygiene or to pharmaceutical or cosmetic preparations, which preparations, in order to achieve a physiological cooling action on the skin and/or mucous membranes, comprise a sufficient amount (1) of a compound according to the invention or a mixture according to the invention (preferably, in a development which is stated to be preferred) or (2) (ii) of a mixture according to the invention (preferably in a development which is stated to be preferred). In particular, the amount used of the compound or mixture should be sufficient to achieve a physiological cooling action on the mucous membranes in the oral, nasal and/or pharyngeal cavities.

Preferred preparations according to the invention comprise conventional basic materials, auxiliary substances and additives for preparations consumed for nutrition or for pleasure or used for oral hygiene or for pharmaceutical or cosmetic preparations. Preferred preparations according to the invention contain 0.0001 wt. % to 20 wt. %, preferably 0.0001 to 10 wt. %, particularly preferably 0.001 wt. % to 0.5 wt. % of compounds of the formula (I), relative to the total weight of the preparation. Further constituents, in particular compounds of the formula (I) and constituents (2) (further substances with physiological cooling action), (3) (aroma substances without a physiological cooling action) and/or (4) (trigeminal or salivatory active substances without a physiological cooling action) (as described above) and further conventional raw materials, auxiliary substances and additives may be included in amounts of from 0.0000001 to 99.99 wt. %, preferably 10 to 80 wt. %, relative to the total weight of the preparation. The preparations according to the invention may furthermore contain water in an amount of up to 99.99 wt. %, preferably of 5 to 80 wt. %, relative to the total weight of the preparation.

Preparations serving for nutrition or pleasure are for example bakery products, (for example bread, dry cookies, cakes, other pastry products), confectionery (for example chocolates, chocolate bar products, other bar products, fruit gums, hard and soft caramels, chewing gum), alcoholic or non-alcoholic beverages (for example coffee, tea, wine, beverages containing wine, beer, beverages containing beer, liqueurs, spirits, liqueurs, brandies, fruit-containing carbonated beverages, isotonic beverages, soft drinks, nectars, fruit and vegetable juices, fruit or vegetable juice preparations), instant beverages (for example instant cocoa beverages, instant tea beverages, instant coffee beverages), meat products (for example ham, fresh or cured sausage preparations, spiced or marinated fresh or cured meat products), eggs or egg products (dried egg, egg white, egg yolk), cereal products (for example breakfast cereals, muesli bars, precooked ready rice products), dairy products (for example milk beverages, milk ice cream, yogurt, kefir, curd cheese, soft cheese, hard cheese, dried milk powder, whey, butter, buttermilk), fruit preparations (for example jams, fruit ice cream, fruit sauces, fruit fillings), vegetable, preparations (for example ketchup, sauces, dried vegetables, deep-frozen vegetables, precooked vegetables, preserved vegetables), snack articles (for example baked or fried potato Chips or potato dough products, maize- or peanut-based extrudates), fat- or oil-based products or emulsions thereof (for example mayonnaise, remoulade, dressings, other ready-to-serve meals and soups (for example dried soups, instant soups, precooked soups), spices, seasoning mixtures and in particular powdered seasonings, which are used for example in snack food applications. The preparations for the purposes of the invention may also be used as semifinished products for the production of further preparations serving for nutrition or for pleasure. The preparations for the purposes of the invention may also be nutritional supplements in the form of capsules, tablets (uncoated and coated tablets, for example coatings resistant to gastric juices), sugar-coated tablets, granules, pellets, mixtures of solids, dispersions in liquid phases, as emulsions, as powders, as solutions, as pastes or as other swallowable or chewable preparations.

Preparations serving for oral hygiene are in particular dental care preparations such as toothpastes, tooth gels, tooth creams, tooth powders, mouthwashes, tooth cream and mouthwash as a 2-in-1 product, dental floss, (sugar-free) chewing gums and other oral care products.

Dental care products (as the basis for preparations serving for oral care) which contain the compounds or mixtures according to the invention generally comprise an abrasive system (abrasive or polishing agent), such as for example silicas, calcium carbonates, calcium phosphates, aluminum oxides and/or hydroxyapatites, surface-active substances such as for example sodium lauryl sulfate, sodium lauryl sarcosinate and/or cocamidopropyl betaine, humectants such as for example glycerol and/or sorbitol, thickeners, such as for example carboxymethylcellulose, polyethylene glycols, carrageenan and/or Laponite®, sweeteners such as for example saccharin, sodium cyclamate, sucralose, acesulfame-K or sugar alcohols, taste-correcting agents for unpleasant taste impressions such as for example hydroxyflavanones according to US 2002/0188019, taste-correcting agents for further, generally not unpleasant taste impressions, taste-modulating substances (for example inositol phosphate, nucleotides such as guanosine monophosphate, adenosine monophosphate or other substances such as sodium glutamate or 2-phenoxypropionic acid), cooling active ingredients such as for example menthol, menthol derivatives (for example L-menthol, L-menthyl lactate, L-menthyl alkylcarbonates, menthone ketals, menthane carboxamides), 2,2,2-trialkylacetamides (for example 2,2-diisopropylpropionic acid methylamide), icilin and icilin derivatives, stabilizers and active ingredients, such as for example sodium fluoride, sodium monofluorophosphate, tin difluoride, quaternary ammonium fluorides, zinc citrate, zinc sulfate, tin pyrophosphate, tin dichloride, blends of different pyrophosphates, triclosan, cetylpyridinium chloride, aluminum lactate, potassium citrate, potassium nitrate, potassium chloride, strontium chloride, hydrogen peroxide, aromas and/or sodium bicarbonate or odor-correcting agents).

Chewing gums (as a further example of the preparations serving for oral care) which contain the compounds or mixtures according to the invention generally comprise a chewing gum base, i.e. a chewable mass which becomes plastic on chewing, sugars of various kinds, sugar substitutes, other sweet-tasting substances, sugar alcohols, taste-correcting agents for unpleasant taste impressions, other taste modulators for further, generally not unpleasant taste impressions, taste-modulating substances (for example inositol phosphate, nucleotides such as guanosine monophosphate, adenosine monophosphate or other substances such as sodium glutamate or 2-phenoxypropionic acid), humectants, thickeners, emulsifiers, aromas and stabilizers or odor-correcting agents.

In the prior art, numerous different chewing gum bases are known, wherein is it necessary to distinguish between "chewing gum" or "bubble gum" bases, wherein the latter are softer, so that chewing gum bubbles may also be formed therewith. These days, in addition to traditionally used natural resins or the natural latex chicle, common chewing-gum bases usually comprise elastomers such as polyvinyl acetates (PVA), polyethylenes, (low or medium molecular weight) polyisobutenes (PIB), polybutadienes, isobutene/isoprene copolymers (butyl rubber), polyvinyl ethyl ether (PVE), polyvinyl butyl ether, copolymers of vinyl esters and vinyl ethers, styrene/butadiene copolymers (styrene/butadiene rubber, SBR), or vinyl elastomers, for example based on vinyl acetate/vinyl laurate, vinyl acetate/vinyl stearate or ethylene/vinyl acetate, and mixtures of the above-stated elastomers, as described for example in EP 0 242 325, U.S. Pat. No. 4,518,615, U.S. Pat. No. 5,093,136, U.S. Pat. No. 5,266,336, U.S. Pat. No. 5,601, 858 or U.S. Pat. No. 6,986,709. In addition, chewing gum bases comprise further constituents such as for example (mineral) fillers, plasticizers, emulsifiers, antioxidants, waxes, fats or fatty oils, such as for example hardened (hydrogenated) plant or animal fats, mono-, di- or triglycerides. Suitable (mineral) fillers are for example calcium carbonate, titanium dioxide, silicon dioxide, talcum, aluminum oxide, dicalcium phosphate, tricalcium phosphate, magnesium hydroxide and mixtures thereof. Suitable plasticizers or agents for preventing adhesion (detackifiers) are for example lanolin, stearic acid, sodium stearate, ethyl acetate, diacetin (glycerol diacetate), triacetin (glycerol triacetate), triethyl citrate. Suitable waxes are for example paraffin waxes, candelilla wax, carnauba wax, microcrystalline waxes and polyethylene waxes. Suitable emulsifiers are for example phosphatides such as lecithin, mono- and diglycerides of fatty acids, for example glycerol monostearate.

Pharmaceutical preparations according to the invention which are preferred for the purposes of the invention are oral preparations, which for example assume the form of capsules, tablets (uncoated and coated tablets, for example coatings resistant to gastric juices), sugar-coated tablets, granules, pellets, mixtures of solids, dispersions in liquid phases, emulsions, powders, solutions, pastes or other swallowable or chewable preparations and are used as prescription-only, drugstore-only or other medicaments or as nutritional supplements.

Cosmetic preparations according to the invention may be present, for example, in one of the following forms: soap, synthetic detergent, liquid washing, shower, or bath preparation, emulsion (as solution, dispersion, suspension, cream, lotion or milk, depending on production, process and constituents, of the type "Water-in-oil" (W/O), "oil-in-water" (O/W) or multiple emulsion, PIT emulsion, emulsion foam, microemulsion, nanoemulsion, Pickering emulsion), ointment, paste, gel (including hydrogel, hydrodispersion gel, oleogel), oil, toner, balsam, serum, powder, eau de toilette, toilet water, eau de cologne, perfume, wax, as a stick, roll-on, (pump) spray, aerosol (foaming, non-foaming or post-foaming), foot care product (including keratolytic preparations, deodorant), beard shampoo or care preparation, insect repellent, sunscreen preparation, aftersun preparation, shaving preparation (for example shaving foams, soaps or gels) or aftershave (balm, lotion), depilatory product, hair care product such as for example shampoo (for example 2-in-1 shampoo, antidandruff shampoo, baby shampoo, shampoo for dry scalp, shampoo concentrate), conditioner, hair tonic, hair lotion, hair rinse, hair cream, pomade, permanent wave and setting lotion, hair smoothing product (defrizzing agent, relaxer), hair strengthener, styling aid (for example gel or wax), blonding product, hair lightener, hair conditioner, hair mousse, hair toning product, hair dye (for example temporary, direct, semipermanent, permanent hair dye), nail care product such as for example nail polish and nail polish remover, deodorant and/or antiperspirant, mouthwash, water pick, make-up, make-up remover, eye care cream, lip cosmetics, lip care preparation, decorative cosmetics (for example powder, eye shadow, kohl pencil, lipstick), bath product (e.g. capsule), or face mask.

Preparations according to the invention which comprise compounds according to the invention or a mixture according to the invention are preferably produced by introducing the compound or the mixture, for example a mixture which comprises a solid or liquid carrier in addition to a compound according to the invention, into a base preparation. Advantageously, mixtures according to the invention present as a solution, which comprise a compound according to the invention, are firstly converted into a solid preparation by spray drying.

According to an alternative preferred embodiment, preparations according to the invention may be produced by incorporating the compounds or mixtures according to the invention, optionally with further constituents of the preparation according to the invention, firstly into emulsions, into liposomes, for example starting from phosphatidyl choline, into microspheres, into nanospheres or also into capsules, granules or extrudates prepared from a matrix suitable for foodstuffs and products consumed for pleasure or cosmetic preparations, for example prepared from starch, starch derivatives (for example modified starch), cellulose or cellulose derivatives (for example hydroxypropylcellulose), other polysaccharides (for example dextrin, alginate, curdlan, carageenan, chitin, chitosan, pullulan), natural fats, natural waxes (for example beeswax, carnauba wax), or from proteins, for example gelatin or other natural products (for example shellac) or non-natural matrix materials (such as polyurea). In said embodiment, depending on the matrix, the products may be treated by spray drying, spray granulation, melt granulation, coacervation, coagulation, extrusion, melt extrusion, emulsion methods, coating or other suitable encapsulation methods and optionally a suitable combination of the above-stated methods.

In a further preferred production method, the compounds or mixtures according to the invention are initially complexed with one or more suitable complexing agents, for example with cyclodextrins or cyclodextrin derivatives, preferably alpha-, beta- or gamma-cyclodextrin, and in used in this complexed form.

A particularly preferred preparation according to the invention is one in which the matrix is selected such that the compounds or mixtures according to the invention, in particular mixtures comprising further cooling active ingredients and/or aromas, are released from the matrix in delayed manner, such that a long-lasting cooling action is achieved.

Further constituents which may be used for preparations according to the invention serving for nutrition or pleasure are conventional basic and auxiliary substances and additives for foodstuffs or products consumed for pleasure, for example water, mixtures of fresh or processed, plant or animal basic or raw materials (for example raw, roasted, dried, fermented, smoked and/or boiled meat, bone, cartilage, fish, vegetables, fruit, herbs, nuts, vegetable or fruit juices or pastes or mixtures thereof), digestible or non-digestible carbohydrates (for example sucrose, maltose, fructose, glucose, dextrins, amylose, amylopectin, inulin, xylans, cellulose, tagatose), sugar alcohols (for example sorbitol, mannitol, erythritol), natural or hardened fats (for example tallow, lard, palm fat, coconut oil, hardened vegetable fat), oils (for example sunflower oil, peanut oil, maize germ oil, olive oil, fish oil, soy oil, sesame oil), fatty acids or the salts thereof (for example potassium stearate), proteinogenic or non-proteinogenic amino acids and related compounds (for example γ-aminobutyric acid, taurine), peptides (for example glutathione), native or processed proteins (for example gelatin), enzymes (for example peptidases), nucleic acids, nucleotides, taste-correcting agents for unpleasant taste impressions, further taste modulators for further, generally not unpleasant taste impressions, other taste-modulating substances (for example inositol phosphate, nucleotides such as guanosine monophosphate, adenosine monophosphate or other substances such as sodium glutamate or 2-phenoxypropionic acid), emulsifiers (for example lecithins, diacylglycerols, gum arabic), stabilizers (for example carageenan, alginate), preservatives, (for example benzoic acid, sorbic acid), antioxidants (for example tocopherol, ascorbic acid), chelating agents (for example citric acid), organic or inorganic acidulants (for example malic acid, acetic acid, citric acid, tartaric acid, phosphoric acid), bitter substances (for example quinine, caffeine, limonin, amarogentin, humulone, lupulone, catechins, tannins), mineral salts (for example sodium chloride, potassium chloride, magnesium chloride, sodium phosphate), substances preventing enzymatic browning (for example sulfite, ascorbic acid), essential oils, plant extracts, natural or synthetic dyes or coloring pigments (for example carotenoids, flavonoids, anthocyans, chlorophyll and the derivatives thereof), spices, trigeminally active substances or plant extracts containing such trigeminally active substances, synthetic, natural or nature-identical aroma substances or odoriferous substances and odor-correcting agents.

A combination of a compound according to the invention or a mixture according to the invention with sugar alcohols, in particular with xylitol, sorbitol, mannitol and/or erythritol exhibited an enhanced, in part synergistically enhanced, cooling action.

Another aspect of the present invention relates to the use of (a) a compound of the formula (I) or (b) a mixture comprising one, two or more compounds of the formula (I) or (c) a mixture consisting of two or more compounds of the formula (I)

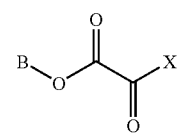

(I)

wherein the following in each case applies:
B means a hydrocarbon residue selected from the following group:

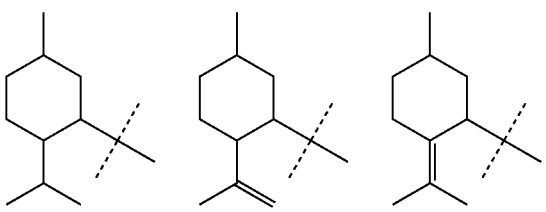

-continued

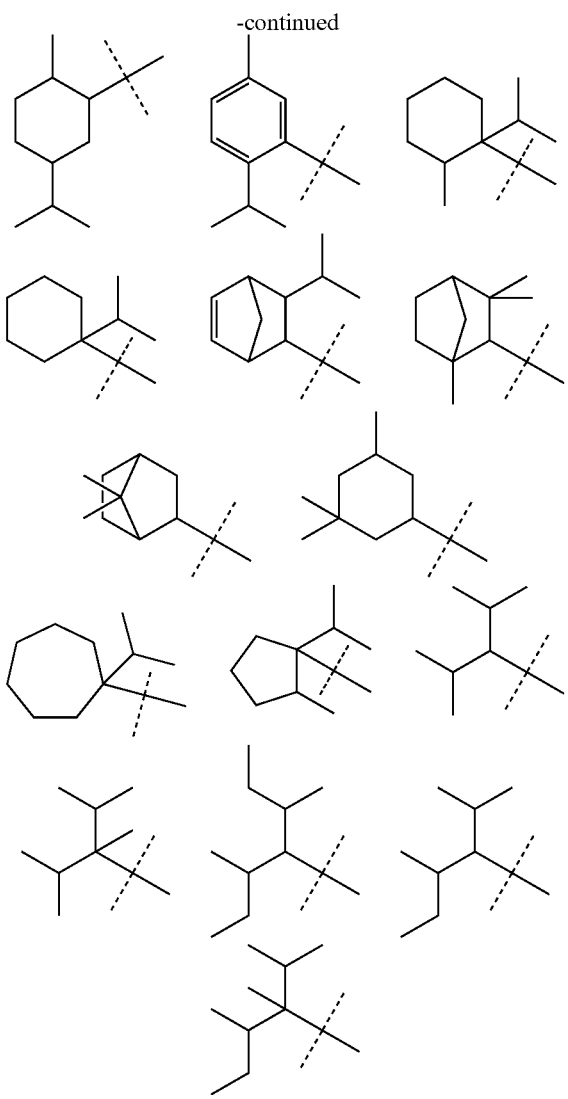

in which the dashed line indicates the bond which links the hydrocarbon residue B with the adjacent oxygen atom in formula (I),
X means $NR^1R^2$ or $SR^3$,
wherein in each case-mutually independently
in $NR^1R^2$ the residues $R^1$ and $R^2$ are selected and
in $SR^3$ the residue $R^3$ is selected
from the group consisting of:
hydrogen
and
organic residue with
1 to 12 C atoms which is
selected from the group consisting of substituted or unsubstituted
alkyl, heteroalkyl, cycloalkyl, heterocycloalkyl, cycloalkylalkyl; alkenyl, cycloalkenyl, cycloalkenylalkyl, alkynyl, cycloalkylalkynyl, aryl, heteroaryl, arylalkyl, cycloalkylaryl, cycloalkenylaryl, cycloalkylheteroaryl, heterocycloalkylaryl, heterocycloalkenylaryl, heterocycloalkenylheteroaryl and heteroarylalkyl,
wherein optionally in $NR^1R^2$ the residues $R^1$ and $R^2$ are covalently bonded together with omission of one hydrogen atom in each case and with formation of a ring
(i) for producing a cooling action on the skin or a mucous membrane for other than therapeutic purposes or
(ii) for producing a medicament.

The above statements regarding mixtures according to the invention apply correspondingly with regard to (a) compounds, (b) mixtures comprising one, two or more compounds of the formula (I) or (c) a mixture consisting of two or more compounds of the formula (I) which are preferably to be used.

The compounds (a) and/or mixtures (b), (c) according to the invention are preferably used to produce a medicament which serves to combat or alleviate coughs, colds, symptoms of oral, nasal, throat or pharyngeal inflammation, sore throat or hoarseness.

A further aspect of the present invention relates to a therapeutic or non-therapeutic method for achieving a physiological cooling action on the skin and/or a mucous membrane, comprising the following step:
applying an amount sufficient to achieve a physiological cooling action
(1) of a compound or a mixture as described above
(2) of a preparation as described above
onto the skin and/or a mucous membrane.

A further aspect of the invention relates to the use of preparations according to the invention containing a compound according to the invention, a mixture according to the invention, preferably a mixture according to the invention which comprises one or more aroma substances and/or one or more further cooling active ingredients (cooling active ingredients which are not a compound of the general formula (I)), as semifinished products ("aroma mixtures") for aromatizing finished, products produced using the semifinished products.

Further aspects of the present invention emerge from the following Examples and the appended claims.

EXAMPLES

The Examples merely serve to illustrate the invention without thereby limiting it. Unless otherwise stated, all stated values relate to weight.

Example 1

Synthesis of L-menthyl methyl oxalate

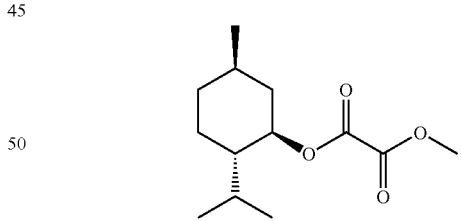

156 g of L-menthol were initially introduced with 116 g of triethylamine in 500 ml of dichloromethane and monomethyl oxalyl chloride was added dropwise at 0° C. within 30 minutes. Stirring was continued for one hour at room temperature and then washing was performed with water. After removal of the solvent, 240 g of the compound were obtained.

$^1$H-NMR (400 MHz, CDCl$_3$, TMS): δ=0.78 (d, J=7.0 Hz, 3H), 0.86-0.96 (m, 1H), 0.91 (d, J=7.0 Hz, 3H), 0.93 (d, J=6.5 Hz, 3H) 1.02-1.19 (m, 2H), 1.46-1.58 (m, 2H), 1.67-1.76 (m, 2H), 1.89 (dhept, J=2.8 Hz, J=7.0 Hz, 1H), 2.02-2.08 (m, 1H), 3.90 (s, 3H), 4.87 (dt, J=11 Hz, J=4.5 Hz, 1H) ppm.

$^{13}$C-NMR (100 MHz, CDCl$_3$, TMS): δ=16.18 (CH$_3$), 20.65 (CH$_3$), 2-1.92 (CH$_3$), 23.35 (CH$_2$), 26.17 (CH), 31.46

(CH), 34.02 (CH$_2$), 40.28 (CH$_2$), 46.72 (CH), 53.46 (CH$_3$), 77.89 (CH), 157.33 (CO), 158.59 (CO) ppm.

MS (EI): m/z=242 (1, M$^+$), 227 (1), 183 (1), 155 (1), 139 (22), 123 (7), 95 (30), 83 (100), 69 (40), 55 (55).

Example 2

Synthesis of L-menthyl N-methyl oxamate

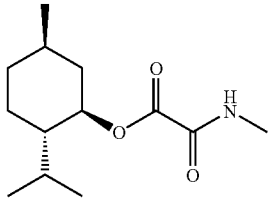 [SMILES: CNC(=O)C(=O)O[C@@H]1C[C@H](C)CC[C@H]1C(C)C]

120 g of L-menthyl methyl oxalate were initially introduced into 1000 ml of diethyl ether and 1.1 equivalents of methylamine were then added dropwise slowly and with constant cooling (0° C.). Stirring was continued for 30 minutes, washing performed with water and, after drying and evaporation, 116 g of crude product were recrystallized from 290 g of heptane. In this manner, 98.1 g of L-menthyl N-methyl oxamate were obtained.

$^1$H-NMR (400 MHz, CDCl$_3$, TMS): δ=0.75 (d, J=7.0 Hz, 3H), 0.85-0.96 (m, 1H), 0.90 (d, J=7.0 Hz, 3H), 0.92 (d, J=6.6 Hz, 3H), 1.01-1.22 (m, 2H), 1.44-1.64 (m, 2H), 1.67-1.75 (m, 2H), 1.90 (dhept, J=7.0 Hz, J=2.8 Hz, 1H), 1.91-2.03 (m, 1H), 2.93 (d, J=5.2 Hz, 3H), 4.83 (dt, J=11 Hz, J=4.5 Hz, 1H), 7.14 (s, br., NH) ppm.

$^{13}$C-NMR (100 MHz, CDCl$_3$, TMS): δ=16.09 (CH$_3$), 20.65. (CH$_3$), 21.94 (CH$_3$), 23.26 (CH$_2$), 26.08 (CH), 26.46 (CH$_3$), 31.50 (CH), 34.03 (CH$_2$), 40:29 (CH$_2$), 46.57 (CH), 77.77 (CH), 157.46 (CO), 160.26 (CO) ppm.

MS (EI): m/z=241 (1, M$^+$), 183 (1), 155 (1), 139 (20), 123 (5), 97 (19), 83 (100), 69 (37), 55 (52).

Example 3

Synthesis of L-menthyl N-ethyl oxamate

In a similar manner to the synthesis of L-menthyl N-methyl oxamate, L-menthyl N-ethyl oxamate was obtained starting from L-menthyl methyl oxalate.

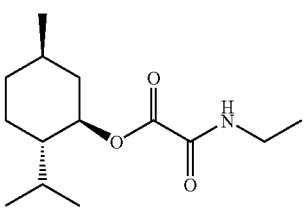 [SMILES: CCNC(=O)C(=O)O[C@@H]1C[C@H](C)CC[C@H]1C(C)C]

$^1$H-NMR (400 MHz, CDCl$_3$, TMS): δ=0.76 (d, J=7.0.Hz, 3H), 0.85-0.96 (m, 1H), 0.90 (d, J=7.0 Hz, 3H), 0.92 (d, J=6.6 Hz, 3H), 1.02-1.22 (m, 2-H), 1.22 (t, J=7.3 Hz, 3H), 1.44-1.64 (m, 2H), 1.66-1.76 (m, 2H), 1.91 (dhept, J=7.0 Hz, J=2.7 Hz, 1H), 1.97-2.04 (m, 1H), 3.35-3.43 (m, 2H), 4.83 (dt, J=11.0 Hz, J=4.5 Hz, 1H), 7.17 (s, br., 1 NH) ppm.

$^{13}$C-NMR (100 MHz, CDCl$_3$, TMS): δ=14.39 (CH$_3$), 16.10 (CH$_3$), 20.65 (CH$_3$), 21.94 (CH$_3$), 23.27 (CH$_2$), 26.05 (CH), 31.50 (CH), 34.03 (CH$_2$), 34.81 (CH$_2$), 40.28 (CH$_2$), 46.55 (CH), 77.70 (CH), 156.65 (CO), 160.48 (CO) ppm.

MS (EI): m/z=255 (1, M$^+$), 168 (1), 155:(1), 139 (20), 123 (5), 97 (20), 83 (100), 69 (37), 55 (50).

Example 4

Synthesis of neomenthyl N-methyl oxamate

In a similar manner to the synthesis of L-menthyl N-methyl oxamate, neomenthyl N-methyl oxamate was obtained starting from neomenthyl methyl oxalate.

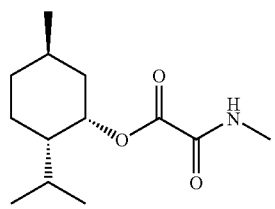 [SMILES: CNC(=O)C(=O)O[C@H]1C[C@H](C)CC[C@H]1C(C)C]

$^1$H-NMR (400 MHz, CDCl$_3$, TMS): δ=0.84-1.16 (m, 4H), 0.85 (d, J=6.6 Hz, 3H), 0.86 (d, J=6.7 Hz, 3H), 0.90 (d, J=6.7 Hz, 3H), 1.43-1.57,(m, 2H), 1.63-1.83 (m, 2H), 1.94-2.01 (m, 1H), 2.92 (d, J=5.2 Hz, 3H), 5.34 (d, br., J=2.1 Hz, 1H), 7.05 (s, br., 1 NH) ppm.

$^{13}$C-NMR (100 MHz, CDCl$_3$, TMS): δ=20.77 (CH$_3$), 20.84 (CH$_3$), 22.04 (CH$_3$), 24.86 (CH$_2$), 26.39 (CH), 26.41 (CH$_3$), 29.05 (CH), 34.60 (CH$_2$), 38.84 (CH$_2$), 46.79 (CH), 74.90 (CH), 157.48 (CO), 160.09 (CO) ppm.

MS (EI): m/z=242 (1, MH$^+$), 182 (1), 155 (1), 139 (25), 123 (5), 95 (20), 83 (100), 69 (45), 55 (55).

Example 5

Synthesis of neomenthyl-N-cyclopropyl oxamate

In a similar manner to the synthesis of L-menthyl N-methyl oxamate, neomenthyl N-cyclopropyl oxamate was obtained starting from neomenthyl methyl oxalate.

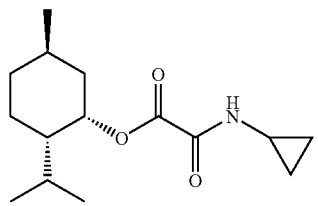 [SMILES: CC(C)[C@@H]1CC[C@@H](C)C[C@@H]1OC(=O)C(=O)NC1CC1]

$^1$H-NMR (400 MHz, CDCl$_3$, TMS): δ=0.60-0.65 (m, 2H), 0.82-1.15 (m, 5H), 0.85 (d, J=6.5 Hz, 3H), 0.86 (d, J=6.7 Hz, 3H), 0.90 (d, J=6.7 Hz, 3H), 1.44-1.57 (m, 2 H), 1.62-1.82 (m, 3H), 1.92-2.00 (m, 1H), 2.77-2.84 (m, 1H), 5.32 (d, br, J=2.1 Hz, 1H), 7.08 (s, br., 1H) ppm.

$^{13}$C-NMR (100 MHz, CDCl$_3$, TMS): δ=6.53 (2×CH$_2$), 20.79 (CH$_3$), 20.83 (CH$_3$), 22.04 (CH$_3$), 22.81 (CH), 24.80 (CH$_2$), 26.35 (CH), 29.00 (CH), 34.61, (CH$_2$), 38.83 (CH$_2$), 46.83 (CH), 74.97 (CH), 157.95 (CO), 160.25 (CO) ppm.

MS (EI): m/z=267 (1, M$^+$), 155 (1), 139 (25), 129 (22), 95 (20), 83 (100), 69 (30), 55 (45).

Example 6

Synthesis of L-menthyl morpholinooxamate (morpholin-4-yl-oxo-acetic acid (1R,2S,5R)-2-isopropyl-5-methylcyclohexyl ester)

In a similar manner to the synthesis of L-menthyl N-methyl oxamate, L-menthyl morpholinooxamate was obtained starting from L-menthyl methyl oxalate.

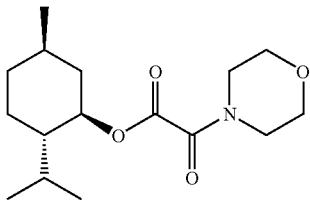 [SMILES: CC(C)[C@@H]1CC[C@@H](C)C[C@H]1OC(=O)C(=O)N1CCOCC1]

$^1$H-NMR (400 MHz, CDCl$_3$, TMS): δ=0.79 (d, J=6.9 Hz, 3H), 0.85-0.95 (m, 1H), 0.91 (d, J=7.0 Hz, 3H), 0.93 (d, J=7.0 Hz, 3H), 1.02-1.16 (m, 2H), 1.46-1.58 (m, 2H), 1.67-1.76 (m, 2H), 1.92 (dhept, J=7.0 Hz, J=2.8 Hz, 1H), 2.03-2.10 (m, 1H), 3.42-3.46 (m, 2H), 3.58-3.77 (m, 6H), 4.86 (dd, J=10.9 Hz, J=4.4 Hz, 1H) ppm.

$^{13}$C-NMR (100 MHz, CDCl$_3$, TMS): δ=16.08 (CH$_3$), 20.68 (CH$_3$), 21.93 (CH$_3$), 23.26 (CH$_2$), 26.12 (CH), 31.48 (CH), 34.01 (CH$_2$), 40.47 (CH$_2$), 41.60 (CH$_2$), 46.33 (CH$_2$), 46.74 (CH), 66.40 (CH$_2$), 66.62 (CH$_2$), 76.79 (CH) 160.49 (CO), 162.30: (CO) ppm.

MS (EI): m/z=297 (2, M$^+$), 160 (1), 139 (15), 114 (14), 97 (20), 83 (100), 69 (30), 55 (35).

Example 7

Synthesis of L-menthyl oxamate

In a similar manner to the synthesis of L-menthyl N-methyl oxamate, L-menthyl oxamate was obtained starting from L-menthyl methyl oxalate.

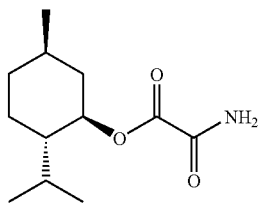 [SMILES: CC(C)[C@@H]1CC[C@@H](C)C[C@H]1OC(=O)C(N)=O]

$^1$H-NMR (400 MHz, CDCl$_3$, TMS): δ=0.77 (d, J=7.1 Hz, 3H), 0.90 (d, J=7.1 Hz, 3H), 0.85-0.97 (m, 1H), 0.93 (d, J=6.7 Hz, 3H), 1.02-1.22 (m, 2H), 1.46-1.63 (m, 2H), 1.67-1.76 (m, 2H), 1.89 (dhept, J=7.0 Hz, J=2.7 Hz, 1H), 1.99-2.05 (m, 1H), 4.85 (dt, J=11.0 Hz, J=4.5 Hz, 1H), 6.23 (s, br. NH), 6.98 (s, br. NH), ppm.

$^{13}$C-NMR (100 MHz, CDCl$_3$, TMS): δ=16.10 (CH$_3$), 20.65 (CH$_3$), 21.92 (CH$_3$), 23.25 (CH$_2$), 26.13 (CH), 31.50 (CH), 34.00 (CH$_2$), 40.28 (CH$_2$), 46.60 (CH), 78.08 (CH), 158.73 (CO), 159.67 (CO) ppm.

MS (EI): m/z=155 (1), 139 (20), 123 (5), 97 (17), 83 (100), 69 (32), 55 (55), 41 (25).

Example 8

Synthesis of bornyl N-ethyl oxamate

In a similar manner to the synthesis of L-menthyl N-methyl oxamate, bornyl N-ethyl oxamate was obtained starting from bornyl methyl oxalate.

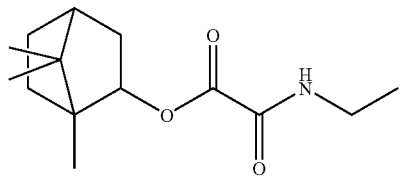 [SMILES: CCNC(=O)C(=O)OC1CC2CCC1(C)C2(C)C]

$^1$H-NMR (400 MHz, CDCl$_3$, TMS): δ=0.88 (s, 3H), 0.9 (s, 3H), 0.93 (s, 3H), 1.11 (dd, J=13.8 Hz, J=3.4 Hz, 1H), 1.22 (t, J=7.3 Hz, 3H), 1.28-1.41 (m, 2H), 1.70-1.81 (m, 2H), 2.04-2.13 (m, 1H), 2.35-2.44 (m, 1H), 3.34-3.43 (m, 2H), 5.01 (ddd, J=10 Hz, J=3.5 Hz, J=2.1 Hz, 1H), 7.06 (s, br., 1 NH) ppm.

$^{13}$C-NMR (100 MHz, CDCl$_3$, TMS): δ=13.49 (CH$_3$), 14.42 (CH$_3$), 18.84 (CH$_3$), 19.68 (CH$_3$), 27.02 (CH$_2$), 27.91 (CH$_2$), 34.77 (CH$_2$), 36.27 (CH$_2$), 44.85 (CH), 48.07 (C), 49.17 (C), 83.18 (CH), 156.58 (CO), 161.26 (CO) ppm.

MS (EI): m/z=253 (2, M$^+$), 225 (3), 197-(10), 181 (10), 153 (52), 137 (70), 121 (23), 109 (21), 95 (98), 81 (100), 41 (25).

Example 9

Synthesis of D-menthyl N,N-dimethyl oxamate

In a similar manner to the synthesis of L-menthyl N-methyl oxamate, D-menthyl N,N-dimethyl oxamate was obtained starting from D-menthyl methyl oxalate.

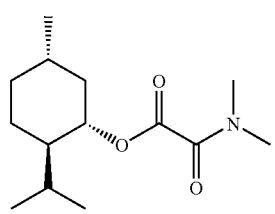 [SMILES: CC(C)[C@H]1CC[C@H](C)C[C@@H]1OC(=O)C(=O)N(C)C]

$^1$H-NMR (400 MHz, CDCl$_3$, TMS): δ=0.80 (d, J=7.0 Hz, 3H), 0.87-0.95 (m, 1H), 0.91 (d, J=7.0 Hz, 3H), 0.93 (d, J=6.5 Hz, 3H), 1.03-1.17 (m, 2H), 1.45-1.59 (m, 2H), 1.67-1.76 (m, 2H), 1.96 (dhept, J=2.8 Hz, J=7.0 Hz, 1H), 2.06-2.12 (m, 1H), 2.98 (s, 3H), 3.01 (s, a H), 4.87 (dt, J=11 Hz, J=44 Hz, 1H) ppm.

$^{13}$C-NMR (100 MHz, CDCl$_3$, TMS): δ=16.03 (CH$_3$), 20.70 (CH$_3$), 21.93 (CH$_3$), 23.23 (CH$_2$), 26.02 (CH), 31.46 (CH), 33.89 (CH$_3$), 34.04 (CH$_2$), 36.98 (CH$_3$), 40.44 (CH$_2$), 46.75 (CH), 76.39 (CH), 162.06 (CO), 162.94 (CO) ppm.

MS (EI): m/z=255 (1, M$^+$), 139 (17), 123 (5), 97 (20), 83 (100), 69 (36), 55 (49).

Example 10

Synthesis of fenchyl N-methyl oxamate

In a similar manner to the synthesis of L-menthyl N-methyl oxamate, fenchyl N-methyl oxamate was obtained starting from fenchyl methyl-oxalate.

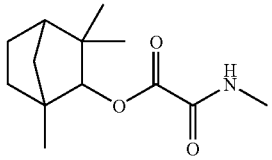 [SMILES: CNC(=O)C(=O)OC1C2(C)CCC(C2)C1(C)C]

$^1$H-NMR (400 MHz, CDCl$_3$, TMS): δ=0.82 (s, 3H), 1.08 (s, 3H), 1.12 (s, 3H), 1.17 (m, 1H), 1.25 (dd, J=10.4 Hz, J=1.6 Hz, 1H), 1.49 (m, 1H), 1.62 (m, 1H), 1.74-1.76 (m, 2H), 1.90 (m, 1H), 2.93 (d, J=5.2 Hz, 3H), 4.48 (d, J=2.0 Hz, 1H), 7.05 (s, br. 1H) ppm.

$^{13}$C-NMR (100 MHz, CDCl$_3$, TMS): δ=19.34 (CH$_3$), 20.20 (CH$_3$), 25.79 (CH$_2$), 26.42 (CH$_3$), 26.53 (CH$_2$), 29.78 (CH$_3$), 39.77 (C), 41.46 (CH$_2$), 48.28 (CH), 48.53 (C), 89.30 (CH), 157.28 (CO), 161.02 (CO) ppm.

MS (EI): m/z=240 (1, MH$^+$), 211 (1) 183 (1), 153 (100), 137 (30), 81 (90), 58 (20).

Example 11

Synthesis of 1-isopropyl-2-methylpropyl N-ethyl oxamate

In a similar manner to the synthesis of L-menthyl N-methyl oxamate, 1-isopropyl-2-methylpropyl N-ethyl oxamate was obtained starting from (1-isopropyl-2-methyl)propyl methyl oxalate.

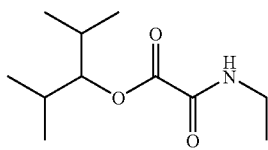

$^1$H-NMR (400 MHz, CDCl$_3$, TMS): δ=0.91 (d, J=6.9 Hz, 6H), 0.92. (d, J=6.7 Hz, 6H), 1.22 (t, J=7.2 Hz, 3H), 2.03 (m, 2H), 3.39 (m, 2H), 4.70 (t, J=6.2 Hz, 1H), 7.06 (s, br., NH) ppm.

$^{13}$C-NMR (100 MHz, CDCl$_3$, TMS): δ=14.43 (CH$_3$), 17.23 (2×CH$_3$), 19.43 (2×CH$_3$), 29.36 (2×CH), 34.80 (CH$_2$), 86.78 (CH), 156.55 (CO), 160.96 (CO) ppm.

MS (EI): m/z=216 (1, MH$^+$), 172 (1), 128 (1), 144 (1), 115 (1), 99 (20), 73 (30), 57 (100), 43 (40).

Example 12

Synthesis of L-menthyl N-2-methoxyethyl oxamate

In a similar manner to the synthesis of L-menthyl N-methyl oxamate, L-menthyl N-2-methoxyethyl oxamate was obtained-starting from L-menthyl methyl oxalate.

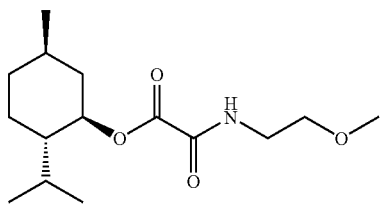 [SMILES: COCCNC(=O)C(=O)O[C@@H]1C[C@H](C)CC[C@H]1C(C)C]

$^1$H-NMR (400 MHz, CDCl$_3$, TMS): δ=0.76 (d, J=7.0 Hz, 3H), 0.85-0.96 (m, 1H), 0.90 (d, J=7.0 Hz, 3H), 0.93 (d, J=6.5 Hz, 3H), 1.02-1.22 (m, 2H), 1.45-1.64 (m, 2H), 1.66-1.76 (m, 2H), 1.90 (dhept, J=2.8 Hz, J=7.0 Hz, 1H), 1.98-2.05 (m, 1H), 3.38 (s, 3H), 3.48-3.57 (m, 4H), 4.83 (dt, J=11.0 Hz, J=4.5 Hz, 1H), 7.42 (s, br., NH) ppm.

$^{13}$C-NMR (100 MHz, CDCl$_3$, TMS): δ=16.15 (CH$_3$), 20.64 (CH$_3$), 21.94 (CH$_3$), 23.30 (CH$_2$), 26.10 (CH), 31.49 (CH), 34.03 (CH$_2$), 39.64 (CH$_2$), 40.27 (CH$_2$), 46.56 (CH), 58.85 (CH$_3$), 70.49 (CH$_2$), 77.79 (CH), 156.87 (CO), 160.17 (CO) ppm.

MS (EI): m/z=286 (1, MH$^+$), 253 (1), 158 (1), 147 (15), 139 (17), 97 (17), 83 (100), 69 (30), 55 (43).

Example of Application 1

Cooling Action

The compounds according to Examples 1 to 12 were tested for their organoleptic properties, in particular their cooling action. To this end, they were dissolved, in each case in a specific final concentration, in a mass prepared from sucrose (saccharose) and water (confectioner's fondant, supplier Nordzucker AG, Nordstemmen) and evaluated by a panel of experts. Sensory impressions were rated and the cooling action was assessed on a scale from 1 (no cooling action) to 9 (extremely strong cooling action). The results were convincing in every case.

The profile of L-menthyl N-methyl oxamate (Example 2) at a concentration of 0.05 wt. %, relative to the complete preparation was described as follows: very slightly bitter, cooling action 6.

Example of Application 2

Aroma Mixture for Achieving a Cooling Action

| Constituent | Proportion in wt. % |
|---|---|
| L-Menthyl N-methyl oxamate (Example 2) | 25 |
| L-Menthyl lactate (Frescolat ML, Symrise) | 50 |
| L-Menthyl 3-oxobutyrate | 15 |
| O-L-Menthyl-O'-(2-hydroxyethyl) carbonate (Frescolat MGC, Symrise) | 10 |

A strongly cooling, but otherwise virtually tasteless and odorless aroma mixture which is liquid at room temperature (20° C.) is obtained by mixing the components.

Example of Application 2A

Aroma Mixture for Achieving a Cooling Action

| Constituent | Proportion in wt. % |
| --- | --- |
| L-Menthyl N-methyl oxamate (Example 2) | 14 |
| Menthane carboxylic acid N-(4-cyanomethylphenyl)amide | 1 |
| Peppermint oil | 30 |
| L-Menthol | 30 |
| L-Menthyl lactate (Frescolat ML, Symrise) | 15 |
| Propylene glycol | 10 |

A strongly cooling but virtually tasteless and odorless aroma mixture is obtained by mixing the components.

Example of Application 3

Aroma Mixture for Achieving a Cooling Action

| Constituent | Proportion in wt. % |
| --- | --- |
| L-Menthyl N-methyl oxamate (Example 2) | 7.5 |
| L-Menthane carboxylic acid N-ethylamide (WS3, for example Millennium) | 5 |
| L-Menthyl lactate (Frescolat ML, Symrise) | 32.5 |
| O-L-Menthyl-O'-(2-hydroxyethyl) carbonate (Frescolat MGC, Symrise) | 5 |
| Propylene glycol | 50 |

A strongly cooling, but otherwise virtually tasteless and odorless aroma mixture which is liquid at room temperature (20° C.) is obtained by mixing the components.

Example of Application 4

Aroma Mixture for Achieving an Aromatizing and Cooling Action

| Constituent | Proportion in wt. % |
| --- | --- |
| L-Menthyl N-methyl oxamate (Example 2) | 15 |
| Peppermint oil | 10 |
| L-Menthol | 40 |
| L-Menthyl lactate (Frescolat ML, Symrise) | 25 |
| O-L-Menthyl-O'-(2-hydroxyethyl) carbonate (Frescolat MGC, Symrise) | 10 |

A strongly cooling aroma blend with a strong odor of peppermint is obtained by blending the components.

Example of Application 5

Aroma Mixture for Achieving a Cooling Action with a Simultaneous Tingling Effect

| Constituent | Proportion in wt. % |
| --- | --- |
| L-Menthyl N-methyl oxamate (Example 2) | 15 |
| Solution of 10 wt. % trans-pellitorine in propylene glycol/peppermint oil 1:1 | 10 |
| L-Menthyl lactate (Frescolat ML, Symrise) | 65 |
| O-L-Menthyl-O'-(2-hydroxyethyl) carbonate (Frescolat MGC, Symrise) | 10 |

A strongly cooling aroma mixture which stimulates salivation and causes a tingling effect is obtained by mixing the components.

Example of Application 6

Use in the Form of an Aroma Mixture in a Toothpaste

| Part | Constituent | I (wt. %) | II (wt. %) |
| --- | --- | --- | --- |
| A | Demineralized water | 22.00 | 22.00 |
|   | Sorbitol (70%) | 45.00 | 45.00 |
|   | Solbrol ® M, sodium salt (Bayer AG, p-hydroxybenzoic acid alkyl ester) | 0.15 | 0.15 |
|   | Trisodium phosphate | 0.10 | 0.10 |
|   | Saccharin, 450x | 0.20 | 0.20 |
|   | Sodium monofluorophosphate | 1.12 | 1.12 |
|   | Polyethylene glycol 1500 | 5.00 | 5.00 |
| B | Sident 9 (abrasive silicon dioxide) | 10.00 | 10.00 |
|   | Sident 22 S (thickening silicon dioxide) | 8.00 | 8.00 |
|   | Sodium carboxymethylcellulose | 0.90 | 0.90 |
|   | Titanium dioxide | 0.50 | 0.50 |
| C | Demineralized water | 4.53 | 4.53 |
|   | Sodium lauryl sulfate | 1.50 | 1.50 |
| D | Aroma mixture from Example of application 2 | 1.00 | — |
|   | Aroma mixture from Example of application 2A | — | 1.00 |

The constituents of parts A and B were in each case individually premixed and in each case thoroughly stirred under a vacuum at 25-30° C. for 30 minutes. Part C was premixed and added to A and B; D was added and the mixture was thoroughly stirred under a vacuum at 25-30° C. for a further 30 minutes. After relieving the vacuum, the toothpaste was ready and could be packaged.

A distinct cooling action could be identified when using the resultant toothpastes.

Example of Application 7

Use as Cooling Active Ingredient in a Sugar-Free Chewing Gum

| Part | Constituent | I (wt. %) | II (wt. %) |
| --- | --- | --- | --- |
| A | Chewing gum base, company "Jagum T" | 30.00 | 30.00 |
| B | Powdered sorbitol | 39.00 | 38.80 |
|   | Isomalt ® (Palatinit GmbH) | 9.50 | 9.50 |

-continued

| Part | Constituent | I (wt. %) | II (wt. %) |
|---|---|---|---|
| | Xylitol | 2.00 | 2.00 |
| | Mannitol | 3.00 | 3.00 |
| | Aspartame ® | 0.10 | 0.10 |
| | Acesulfame ® K | 0.10 | 0.10 |
| | Emulgum ® (Colloides Naturels, Inc.) | 0.30 | 0.30 |
| C | Sorbitol, 70% | 14.00 | 14.00 |
| | Glycerol | 1.00 | 1.00 |
| D | Spearmint/peppermint/eucalyptus aroma, containing 5 wt. % L-menthyl N-methyl oxamate (Example 2) | 1.00 | — |
| | Aroma mixture from Example of application 2A | — | 1.20 |

Parts A to D were mixed and vigorously kneaded. The crude mixture was processed into ready-to-use chewing gum, for example in the form of thin strips.

A distinct cooling action could be identified when using the resultant chewing gum.

Example of Application 8

Use as Cooling Active Ingredient in a Mouthwash

| Part | Constituent | Amount used in wt. % |
|---|---|---|
| A | Ethanol | 10.00 |
| | Cremophor ® CO 40 (BASF, detergent) | 1.00 |
| | Benzoic acid | 0.12 |
| | Peppermint/lemon balm aroma, containing 0.4 wt. % pellitorine and 10 wt. % L-menthyl N-methyl oxamate (Example 2) | 0.25 |
| B | Demineralized water | 83.46 |
| | Sorbitol, 70% | 5.00 |
| | Sodium saccharin 450 | 0.07 |
| | L-Blue 5000 e.c., 1% in water (dye) | 0.10 |

The constituents of parts A and B were in each case individually mixed. Part B was slowly stirred into part A until the mixture was homogeneous.

A distinct cooling action could be identified when using the resultant mouthwash.

Example of Application 9

Throat Candies with Liquid/Viscous Core Filling (Center-Filled Hard Candy)

| | I (wt. %) | II (wt. %) |
|---|---|---|
| Mixture A (shell) (80% of the candies) | | |
| Sugar (sucrose) | 58.12 | 49.37 |
| Glucose syrup (solids content 80%) | 41.51 | 49.37 |
| Aroma blend from Example of application 5 | 0.17 | 0.25 |
| l-Menthol | 0.10 | — |
| Lemon oil | 0.10 | 0.10 |
| Citric acid | — | 0.91 |
| Total: | 100 | 100 |
| Mixture B (core) (20% of the candies) | | |
| High fructose maize syrup (sugar solids content 85%, only 15% water) | 84.38 | 84.36 |
| Glycerol | 15.0 | 15.0 |
| Lecithin | 0.02 | 0.02 |
| Cinnamon oil | — | 0.32 |
| Spearmint oil | 0.28 | — |
| Capsaicin | 0.05 | — |
| Vanillyl alcohol n-butyl ether | — | 0.10 |
| Red dye, as 5% aqueous solution | 0.20 | 0.20 |
| Vanillin | 0.07 | — |
| Total | 100 | 100 |

Candies with a liquid/viscous core were produced on the basis of the methods described in U.S. Pat. No. 6,432,441 (Example 1 therein) and those described in U.S. Pat. No. 5,458,894 or U.S. Pat. No. 5,002,791. The two mixtures A and B were separately processed to form bases for the shell (mixture A) or core (mixture B). When consumed by affected individuals, the filled throat candies obtained by means of coextrusion were effective against coughing, sore throat and hoarseness.

Example of Application 10

Chewing Gum

Chewing gum base K2 consisted of the following ingredients: 28.5% terpene resin, 33.9% polyvinyl acetate (MW=14,000), 16.25% hydrogenated vegetable oil, 5.5% mono- and diglycerides, 0.5% polyisobutene (MW 75,000), 2.0% butyl rubber (isobutene/isoprene copolymer), 4.6% amorphous silicon dioxide (water content approx. 2.5%), 0.65% antioxidant tert.-butylhydroxytoluene (BHT), 0.2% lecithin, and 8.5% calcium carbonate. Chewing gum base K2 and the chewing gum were produced in a similar manner to U.S. Pat. No. 6,986,907.

| | I (wt. %) | II (wt. %) | III (wt. %) |
|---|---|---|---|
| Chewing gum base K2 | 25.30 | 27.30 | 26.30 |
| Sorbitol | 61.48 | 59.48 | 61.80 |
| Glycerol | 2.40 | 2.40 | 2.40 |
| Lecithin | 7.00 | 7.00 | 7.00 |
| Aspartame | 0.14 | 0.14 | 0.14 |
| Encapsulated aspartame | 0.68 | 0.68 | 0.68 |
| Menthol, spray-dried | 0.50 | — | — |
| Cherry aroma, spray-dried | — | 1.20 | — |
| Aroma blend from Example of application 4, spray-dried | 1.50 | 1.80 | — |
| Aroma blend from Example of application 3 | 1.00 | — | 1.68 |

The chewing gums of formulations (I) and (II) were shaped into strips, the chewing gum of formulation (III) was shaped into pellets.

A distinct cooling action could be identified when using the resultant chewing gum.

Example of Application 11

Gelatin Capsules for Direct Consumption

|  | I (wt. %) | II (wt. %) | III (wt. %) |
|---|---|---|---|
| Gelatin shell: | | | |
| Glycerol | 2.014 | 2.014 | 2.014 |
| Gelatin 240 Bloom | 7.91 | 7.91 | 7.91 |
| Sucralose | 0.065 | 0.065 | 0.065 |
| Allura Red | 0.006 | 0.006 | 0.006 |
| Brilliant blue | 0.005 | 0.005 | 0.005 |
| Core composition: | | | |
| Vegetable oil triglyceride (coconut oil fraction) | 79.39 | 68.40 | 58.25 |
| Cinnamon/aniseed aroma | 10.00 | 20.90 | — |
| Aroma X | — | — | 29.95 |
| Neotame and aspartame | 0.01 | 0.05 | — |
| Sucralose | 0.22 | 0.30 | 0.70 |
| Aroma blend from Example of application 5 | 0.33 | — | — |
| Aroma blend from Example of application 3 | — | 0.20 | 0.60 |
| L-Menthyl N-methyl oxamate (Example 2) | — | 0.05 | — |
| (−)-Menthone glycerol acetal (Frescolat MGA) | — | 0.10 | 0.40 |
| Vanillin | 0.05 | — | 0.10 |

Aroma X was of the following composition (values in each case in wt. %): 0.1% neotame powder, 0.05% aspartame, 29.3% peppermint arvensis oil, 29.3% peppermint piperita oil Willamette, 2.97% sucralose, 2.28% triacetin, 5.4% diethyl tartrate, 12.1% peppermint oil yakima, 0.7% ethanol, 3.36% 2-hydroxyethyl menthyl carbonate, 3.0% 2-hydroxypropyl menthyl carbonate 5.77% D-limonene, 5.67% L-menthyl acetate.

Gelatin capsules I, II, II suitable for direct consumption were produced according to WO 2004/050069 and in each case had a diameter of 5 mm, the weight ratio of core material to shell material being 90:10. The capsules in each case opened in the mouth within less than 10 seconds and dissolved completely within less than 50 seconds. A distinct cooling action could be identified on chewing and consuming the gelatine capsules produced in this manner.

Example of Application 12

Chewable Candy

|  |  | wt. % |
|---|---|---|
| Water | | 7.80% |
| Sugar | Confectioner's sugar C4 | 42.10% |
| Glucose syrup | Dextrose 40 | 37.30% |
| Hardened vegetable fat | Melting point 32-36° C. | 6.60% |
| Lecithin | Emulsifier (soy lecithin) | 0.30% |
| Gelatin | pig gelatin | 0.80% |
| Fondant | Type-S30 | 4.80% |
| Raspberry aroma | | 0.22% |
| Aroma blend from Example of application 3 | | 0.08% |

Manufacturing instructions:
a) allow gelatin to swell in water (1.8 times the amount of gelatin) at 70° C. for 2 hours;
b) boil sugar, syrup, water, fat and lecithin at 123° C.;
c) slowly mix gelatin solution with the boiled batch;
d) stir in aroma from Example 2 and optionally color;
e) leave the resultant mass to adjust to approx. 70° C. on a cooling table, then add fondant and aerate for approx. 3 minutes on a pulling machine;
f) then chop and package the chewable candy mass.

When the chewable candy is consumed, a fresh, cooling raspberry taste is perceived during chewing.

Example of Application 13

Extrudate

| Glucose syrup, spray-dried (DE value: 31-34) | Glucidex IT33W (from Roquette) | 62.0% |
|---|---|---|
| Maltodextrin (DE value: 17-20) | (from Cerestar) | 28.4% |
| Monomuls emulsifier | Emulsifier based on hardened palm oil; melting point: 64° C. (from Grünau) | 1.8% |
| Dextrose monohydrate (DE value: 99.5) | Dextrose, containing water of crystallization (from Cerestar) | 1.8% |
| Water | | 2.0% |
| Orange/vanilla aroma | | 3.2% |
| Aroma blend from Example of application 4 | | 0.8% |

Manufacturing instructions (see also WO 03/092412):

All constituents were mixed and conveyed into an extruder by single point apportionment. Extrusion temperatures were between 100 and 120° C., specific energy input being 0.2 kWh/kg. The strands emerging from the die plate, which is provided with 1 mm holes, were chopped by rotating blades into approx. 1 mm diameter particles immediately on leaving the die.

Example of Application 14

Fluidized Bed Granules

A solution consisting of 44 wt. % water, 8 wt. % lemon aroma, 3 wt. % aroma mixture from Example of application 4, 13 wt. % gum arabic and 32 wt. % hydrolyzed starch (maltodextrin DE 15-19) and a little green dye is granulated in a granulating apparatus of the type presented in EP 163 836 (with the following features: diameter of distributor base plate: 225 mm, spray nozzle: two-fluid nozzle; pneumatic classifying discharge: zig-zag pneumatic classifier; filter; internal bag filter). The solution is sprayed into the fluidized bed granulator at a temperature of 32° C. The bed contents are fluidized by blowing in nitrogen in an amount of 140 kg/h. The inlet temperature of the fluidizing gas is 140° C. The temperature of the exhaust gas is 76° C. The pneumatic classifying gas used is likewise nitrogen in an amount of 15 kg/h with a temperature of 50° C. The contents of the fluidized bed amounts to approx. 500 g. Granulation output amounts to approx. 2.5 kg per hour. Free-flowing granules are obtained having an average particle diameter of 360 micrometers. The granules are round and exhibit a smooth surface. On the basis of the constant pressure drop of the filter and of the likewise constant bed contents, steady-state conditions may be assumed to prevail with regard to the granulation process.

Example of Application 15

Tea Bag with Rooibos or Black Tea and Extrudates from Example of Application 13, or Granules from Example of Application 14

800 g portions of red bush tea (rooibos tea) were mixed in one case, with 33 g of the extrudates from Example of application 13 and in one case with 30 g of granules from Example of application 14, portioned and then packaged in tea bags. 800 g portions of black tea (leaf grade: fannings) were mixed in one case with 33 g of the extrudates from Example of application 13 and in one case with 30 g of granules from Example of application 14, portioned and then packaged in tea bags.

The effects found in the Example of application may be transferred, optionally by means of modifications which may straightforwardly be carried out by a person skilled in the art, to any product of the relevant product group, i.e., in particular to toothpastes, chewing gums, mouthwashes, throat candies, gelatin capsules, chewable candies and tea in bags. It will be immediately obvious to a person skilled in the art that the compounds and mixtures according to the invention, optionally with slight modifications, are interchangeable without major effort. This means that the compound according to the invention used in the products of the Examples of application must also be considered to represent the other compounds and mixtures according to the invention. The concentration of the compound or mixture used according to the invention may also be varied in a manner which is straightforwardly obvious to a person skilled in the art. Moreover, the further, product-specific constituents in the particular Example of application may likewise straightforwardly be replaced or supplemented by further typical product constituents by a person skilled in the art. Numerous such product-specific constituents are disclosed in the above-stated description.

Example of Application 16

Ready-to-Use Mouthwash with Fluoride and Efficacy Against Bad Breath

|  | I (%) | II (%) | III (%) |
|---|---|---|---|
| Ethanol | 7.00 | 7.00 | 7.00 |
| Glycerol | 12.00 | 12.00 | 12.00 |
| Na fluoride | 0.05 | 0.05 | 0.05 |
| Pluronic F-127 ® (BASF, surface-active substance) | 1.40 | 1.40 | 1.40 |
| Na phosphate buffer pH 7.0 | 1.10 | 1.10 | 1.10 |
| Sorbic acid | 0.20 | 0.20 | 0.20 |
| Na saccharinate | 0.10 | 0.10 | 0.10 |
| Peppermint aroma | 0.15 | 0.15 | 0.10 |
| beta-Homocyclocitral | 0.01 | 0.02 | 0.03 |
| Aroma mixture from Example of application 3 | 0.05 | 0.10 | 0.15 |
| Dye | 0.01 | 0.01 | 0.01 |
| Water, dist. | Ad 100.00 | Ad 100.00 | Ad 100.00 |

Example of Application 17

Gel Tooth Cream with Activity Against Bad Breath

|  | I (%) | II (%) | III (%) |
|---|---|---|---|
| Na carboxymethylcellulose | 0.40 | 0.40 | 0.40 |
| Sorbitol 70%, in water | 72.00 | 72.00 | 72.00 |
| Polyethylene glycol (PEG) 1500 | 3.00 | 3.00 | 3.00 |
| Na saccharinate | 0.07 | 0.07 | 0.07 |
| Na fluoride | 0.24 | 0.24 | 0.24 |
| p-Hydroxybenzoic acid (PHB) ethyl ester | 0.15 | 0.15 | 0.15 |
| Aroma X (see Example of application 11, above) | 0.90 | 0.80 | 0.55 |
| Aroma Z | 0.05 | 0.10 | 0.10 |
| Abrasive silica | 11.00 | 11.00 | 11.00 |
| Thickening silica | 6.00 | 6.00 | 6.00 |
| Sodium dodecyl sulfate (SDS) | 1.40 | 1.40 | 1.40 |
| Aroma mixture from Example of application 5 | 0.10 | 0.25 | 0.30 |
| Blue microcapsules according to U.S. Pat. No. 6 506 368 | — | 0.15 | 0.50 |
| Water, dist. | Ad 100.00 | Ad 100.00 | Ad 100.00 |

Aroma Z: eugenol acetate, beta-homocyclocitral, is isoeugenol methyl ether, farnesol (50:1:30:10 (wt./wt.))

Example of Application 18

Tooth Cream Against Plaque with Efficacy Against Bad Breath

|  | I (%) | II (%) | III (%) |
|---|---|---|---|
| Na carboxymethylcellulose | 1.00 | 1.00 | 1.00 |
| Glycerol | 12.50 | 12.50 | 12.50 |
| Sorbitol 70%, in water | 29.00 | 29.00 | 29.00 |
| Na saccharinate | 0.20 | 0.20 | 0.20 |
| Na fluoride | 0.22 | 0.22 | 0.22 |
| Azacycloheptane-2,2-diphosphoric acid, disodium salt | 1.00 | 1.00 | 1.00 |
| Bromochlorophene | 0.10 | 0.10 | 0.10 |
| Peppermint aroma | 0.90 | 1.00 | 1.00 |
| Aroma mixture from Example of application 4 | 0.10 | 0.20 | 0.30 |
| Parsley seed oil | 0.15 | 0.10 | 0.05 |
| Abrasive silica | 15.00 | 15.00 | 15.00 |
| Thickening silica | 5.00 | 5.00 | 5.00 |
| Sodium dodecyl sulfate (SDS) | 1.50 | 1.50 | 1.50 |
| Water, dist. | Ad 100.00 | Ad 100.00 | Ad 100.00 |

Example of Application 19

Tooth Cream for Sensitive Teeth

|  | I (%) | II (%) | III (%) |
|---|---|---|---|
| Na carboxymethylcellulose | 0.70 | 0.70 | 0.70 |
| Xanthan gum | 0.50 | 0.50 | 0.50 |
| Glycerol | 15.00 | 15.00 | 15.00 |
| Sorbitol 70%, in water | 12.00 | 12.00 | 12.00 |
| K nitrate | 5.00 | 5.00 | 5.00 |
| Na monofluorophosphate | 0.80 | 0.80 | 0.80 |
| PHB methyl ester | 0.15 | 0.15 | 0.15 |

-continued

|  | I (%) | II (%) | III (%) |
|---|---|---|---|
| PHB propyl ester | 0.05 | 0.05 | 0.05 |
| Na saccharinate | 0.20 | 0.20 | 0.20 |
| Aroma X (see Example of application 11, above) | 1.00 | 0.90 | 0.65 |
| Aroma mixture from Example of application 3 | 0.10 | 0.25 | 0.45 |
| Ca carbonate | 35.00 | 35.00 | 35.00 |
| Silicon dioxide | 1.00 | 1.00 | 1.00 |
| Sodium dodecyl sulfate (SDS) | 1.50 | 1.50 | 1.50 |
| Water, dist. | Ad 100.00 | Ad 100.00 | Ad 100.00 |

Example of Application 20

Non-Stick Chewing Gum

Chewing gum base K1 consisted of 2.0% butyl rubber (isobutene/isoprene copolymer, MW 400000), 6.0% polyisobutene (MW=43800), 43.5% polyvinyl acetate (MW=12000), 31.5% polyvinyl acetate (MW=47000), 6.75% triacetin and 10.25% calcium carbonate. Chewing gum base K1 and the chewing gums may be produced in a similar manner to U.S. Pat. No. 5,601,858.

|  | I (wt. %) | II (wt. %) | III (wt. %) |
|---|---|---|---|
| Chewing gum base K1 | 26.00 | 26.00 | 26.00 |
| Triacetin | 0.25 | 0.25 | 0.25 |
| Lecithin | 0.50 | 0.50 | 0.50 |
| Sorbitol, crystalline | Ad 100 | Ad 100 | Ad 100 |
| Mannitol | 15.30 | 15.20 | 15.10 |
| Glycerol | 12.10 | 12.00 | 11.80 |
| Aspartame | 0.17 | 0.17 | 0.17 |
| Encapsulated aspartame | 1.08 | 1.08 | 1.08 |
| Amorphous silica | 1.00 | 1.00 | 1.00 |
| Cottonseed oil | 0.50 | 0.50 | 0.50 |
| Polyoxyethylene sorbitan monolaurate (E-432) | 1.00 | 1.00 | 1.00 |
| Encapsulated spearmint aroma (contains L-carvone) | 0.20 | 0.10 | 0.20 |
| Encapsulated wintergreen aroma (contains methyl salicylate) | — | 0.20 | — |
| Aroma mixture from Example of application 3 | 1.00 | 1.40 | 1.70 |

Example of Application 21

Aroma Mixture for Achieving a Cooling Action

| Constituent | I (wt. %) | II (wt. %) |
|---|---|---|
| L-Menthyl N-methyl oxamate (Example 2) | 75 | 50 |
| Menthane carboxylic acid N-(4-methoxyphenyl)amide [WS12] | 25 | 50 |

The above two cooling active, ingredient building blocks (I) and (II) were incorporated at rate of addition of 0.30 wt. %, 0.50 wt. % and 0.70 wt. % into chewing gums, sugar-free chewing gums, tooth creams, tooth gels and mouthwash concentrates.

Example of Application 22

Tooth Cream and Mouthwash as a 2-in-1 Product

|  | I (wt. %) | II (wt. %) |
|---|---|---|
| Sorbitol | 40.00 | 45.00 |
| Glycerol | 20.00 | 20.00 |
| Ethanol | 5.00 | — |
| Water | Ad 100 | Ad 100 |
| Solbrol M, sodium salt (methylparaben, sodium salt) | 0.15 | 0.15 |
| Na monofluorophosphate | 0.75 | 0.75 |
| Saccharin | 0.20 | 0.20 |
| Sident 9 (abrasive silicon dioxide) | 20.00 | 20.00 |
| Sident 22 S (thickening silicon dioxide) | 2.00 | 2.00 |
| Sodium carboxymethylcellulose | 0.30 | 0.30 |
| Sodium lauryl sulfate (SDS) | 1.20 | 1.20 |
| Color (1% in water) | 0.50 | 0.30 |
| Aroma X from Example of application 11 | 0.90 | — |
| Aroma mixture from Example of application 2 | 0.30 | — |
| Aroma mixture from Example of application 4 | — | 1.00 |

Specific Embodiments

Specific embodiment one comprises (a) A compound of the formula (I) or (b) a mixture comprising one, two or more compounds of the formula (I) or (c) a mixture consisting of two or more compounds of the formula (I)

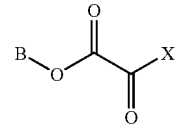

(I)

wherein the following in each case applies:

B means a hydrocarbon residue selected from the following group:

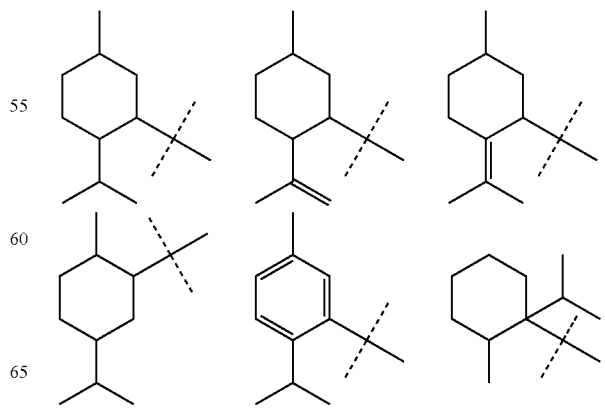

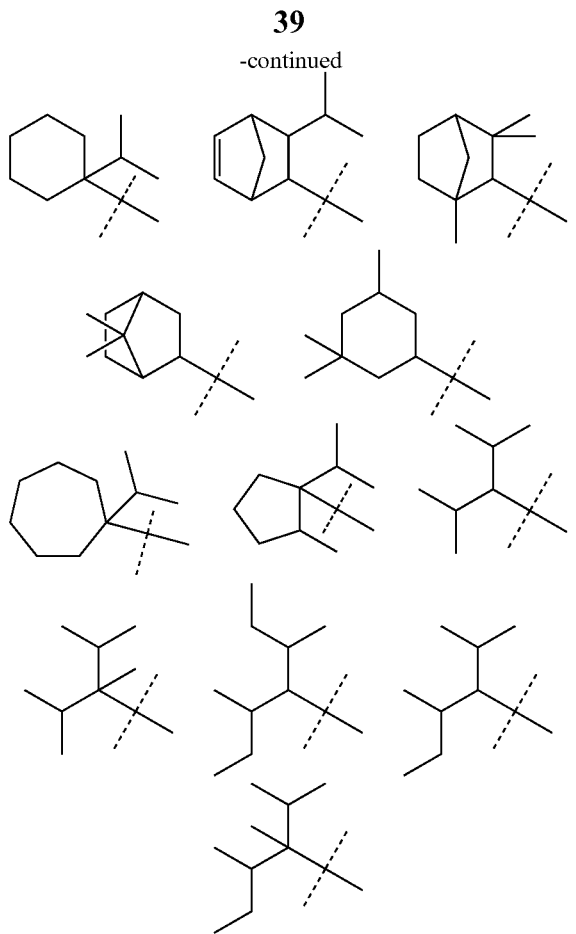

in which the dashed line indicates the bond which links the hydrocarbon residue B with the adjacent oxygen atom in formula (I), X means NR$^1$R$^2$ or SR$^3$,
  wherein in each case mutually independently
  in NR$^1$R$^2$ the residues R$^1$ and R$^2$ are selected and
  in SR$^3$ the residue R$^3$ is selected
  from the group consisting of:
  hydrogen
  and
  organic residue with
  1 to 12 C atoms
    wherein optionally in NR$^1$R$^2$ the residues R$^1$ and R$^2$ are covalently bonded together with omission of one hydrogen atom in each case and with formation of a ring, providing that in the above case (a) the compound of the formula (I) and in case (b) at least one compound of the formula (I) is not selected from the group consisting of:

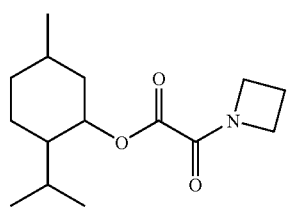

A

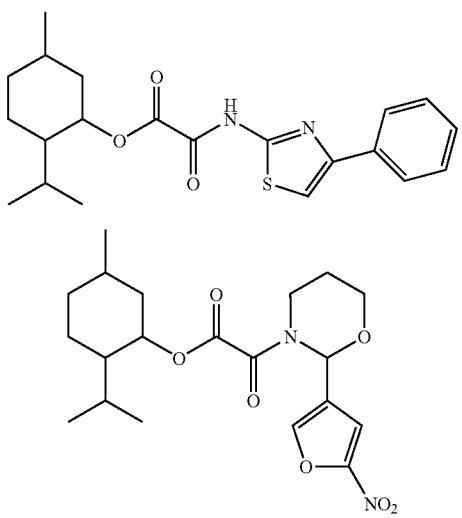

Specific embodiment two comprises (a) The compound of the formula (I) or (b) the mixture comprising one, two or more compounds of the formula (I) or (c) the mixture consisting of two or more compounds of the formula (I): as in specific embodiment one, wherein in case (a) the compound or in case (b) or (c) at least one of the compounds in the mixture is selected from the group consisting of compounds of the formula (I), wherein the following applies:

X means NR$^1$R$^2$ or SR$^3$,
wherein in each case mutually independently
in NR$^1$R$^2$ the residues R$^1$ and R$^2$ are selected and
in SR$^3$ the residue R$^3$ is selected
from the group consisting of:
hydrogen
and
organic residue with
1 to 12 C atoms and
optionally up to 3 heteroatoms, which are in each case mutually independently selected from the group consisting of N, S and O, wherein optionally present heteroatoms from the group consisting of O and S are not covalently bonded to other heteroatoms from this group,
wherein a number of hydrogen atoms attached to C is optionally replaced by fluorine,
wherein the organic residue in each case including all optionally present substituents contains no further heteroatoms from the group consisting of N, S and O as C atoms and is selected from the group consisting of substituted or unsubstituted
C$_1$-C$_{10}$ alkyl, C$_1$-C$_{10}$ heteroalkyl, C$_2$-C$_{10}$ heterocycloalkyl, C$_3$-C$_{10}$ cycloalkyl, C$_4$-C$_{10}$ cycloalkylalkyl, C$_2$-C$_{10}$ alkenyl, C$_3$-C$_{10}$ cycloalkenyl, C$_4$-C$_{10}$ cycloalkenylalkyl, C$_2$-C$_{10}$ alkynyl, C$_5$-C$_{10}$ cycloalkylalkynyl, C$_3$-C$_{10}$ aryl, C$_2$-C$_{10}$ heteroaryl, C$_4$-C$_{10}$ arylalkyl, C$_8$-C$_{10}$ cycloalkylaryl, C$_8$-C$_{10}$ cycloalkenylaryl, C$_5$-C$_{10}$ cycloalkylheteroaryl, C$_8$-C$_{10}$ heterocycloalkylaryl, C$_8$-C$_{10}$ heterocycloalkenylaryl, C$_8$-C$_{10}$ heterocycloalkenylheteroaryl and C$_3$-C$_{10}$ heteroarylalkyl,
and is preferably selected from the group consisting of substituted or unsubstituted C$_1$-C$_8$ alkyl, C$_2$-C$_8$ heteroalkyl, C$_1$-C$_8$ heterocycloalkyl, C$_3$-C$_8$ cycloalkyl, C$_4$-C$_8$ cycloalkylalkyl, C$_2$-C$_8$ alkenyl, C$_3$-C$_8$ cycloalkenyl, C$_4$-C$_8$ cycloalkenylalkyl, C$_3$-C$_6$ aryl, C$_2$-C$_6$ heteroaryl, C$_4$-C$_8$ arylalkyl,
wherein optionally in NR$^1$R$^2$ the residues R$^1$ and R$^2$ are covalently bonded together with omission of one hydrogen atom in each case and with formation of a ring.

Specific embodiment three comprises (a) The compound of the formula (I) or (b) the mixture comprising one, two or more compounds of the formula (I) or (c) the mixture consisting of two or more -compounds of the formula (I) as in any one of the preceding specific embodiments, wherein in case (a) the compound or in case (b) or (c) at least one of the compounds in the mixture is selected from the group consisting of compounds of the formula (I), wherein the following applies:

X means $NHR^1$ wherein $R^1$ has the meaning stated in specific embodiments one to two.

Specific embodiment four comprises (a) The compound of the formula (I) or (b) the mixture comprising one, two or more compounds of the formula (I) or (c) the mixture consisting of two or more compounds of the formula (I), as in any one of the preceding specific embodiments, wherein in case (a) the compound or in case (b) or (c) at least one of the compounds in the mixture is selected from the group consisting of compounds of the formula (i), wherein the following applies:

B means a hydrocarbon residue selected from the group consisting of:

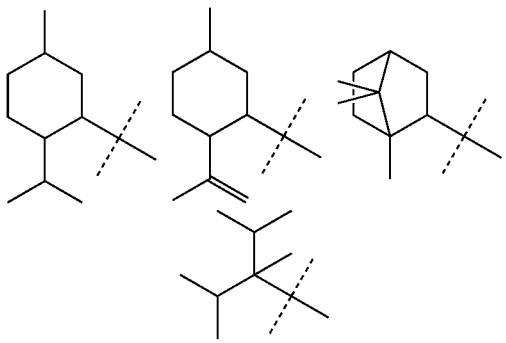

Specific embodiment five comprises (a) The compound of the formula, (I) or (b) the mixture comprising one, two or more compounds of the formula (I) or (c) the mixture consisting of two or more compounds of the formula (I), as in any one of the preceding specific embodiments, wherein in case (a) the compound or in case (b) or (c) at least one of the compounds in the mixture is selected from the group consisting of compounds of the formula (I), wherein the following applies:

B means a hydrocarbon residue selected from the following group:

L-menthyl, D-menthyl or rac-menthyl.

Specific embodiment six comprises. (a) The compound of the formula (I) or (b) the mixture comprising one, two or more compounds of the formula (I) or (c) the mixture consisting of two or more compounds of the formula (I) as in any one of the preceding specific embodiments, wherein in case (a) the compound or in case (b) or (c) at least one of the compounds in the mixture is selected from the group consisting of compounds of the formula (I), wherein the optionally present substituents of the optionally present residues $R^1$, $R^2$ and $R^3$ are mutually independently selected from the group consisting of:

$C_1$-$C_5$ alkyl, $C_3$-$C_8$ cycloalkyl, $C_2$-$C_4$ alkenyl, $C_2$-$C_4$ alkynyl, propynyl, $C_1$-$C_4$ perfluoroalkyl, hydroxy, $C_1$-$C_8$ alkoxy, $C_3$-$C_8$ cycloalkoxy, $C_1$-$C_4$ acyl, $C_1$-$C_4$ alkoxycarbonyl, $C_1$-$C_4$ acyloxy or $C_2$-$C_7$ heteroalkyl and are preferably selected from the group consisting of: methyl, ethyl, n-propyl, iso-propyl, n-butyl, iso-butyl, tert.-butyl, cyclopropyl, cyclopentyl, cyclohexyl, cyclooctyl, ethenyl, propenyl, ethynyl, propynyl, trifluoromethyl, methoxy, ethoxy, iso-propoxy, n-butoxy, iso-butoxy, tert.-butoxy, $C_3$ cycloalkoxy, $C_5$ cycloalkoxy, $C_6$ cycloalkoxy, $C_8$ cycloalkoxy, —[—O—$CH_2$—$CH_2$—]$_v$-Q or —[—O—$CH_2$—CHMe—]$_v$-Q, wherein Q=OH or is $CH_3$ and wherein v may mean 1 or 2, acetyl, $CO_2$Me, $CO_2$Et, $CO_2$iso-Pr, $CO_2$tert.-Bu, acetyloxy, Specific embodiment seven comprises (a) The compound of the formula (I) or (b) the mixture comprising one, two or more compounds of the formula (I) or (c) the mixture consisting of two or more compounds of the formula (I) as in any one of the preceding specific embodiments, wherein in case. (a) the compound or in case (b) or (c) at least one of the compounds in the mixture is selected from the group consisting of compounds of the formula (I), wherein the residues $R^1$ and $R^2$ of the group $NR^1R^2$ are covalently bonded together with omission of one hydrogen atom in each case and form an at most 7-membered ring and preferably form a group $NR^1R^2$ which is selected from the group consisting of piperidinyl and morpholinyl.

Specific embodiment eight comprises (a) The compound of the formula (I) or (b) the mixture comprising one, two or more compounds of the formula (I) or (c) the mixture consisting of two or more compounds of the formula (I) as in any one of the preceding specific embodiments; wherein in case (a) the compound or in case (b) or (c) at least one of the compounds in the mixture is selected from the group consisting, of compounds of the formula (I), wherein the following applies:

B means a hydrocarbon residue selected from the group consisting of:

L-menthyl, D-menthyl or rac-menthyl

X means $NR^1R^2$ wherein in each case mutually independently the residues $R^1$ and $R^2$ are selected from the group consisting of:

hydrogen
and
organic residue with
1 to 12 C atoms and
optionally up to 3 heteroatoms, which are in each case mutually independently selected from the group consisting of N, S and O, wherein optionally present heteroatoms from the group consisting of O and S are not covalently bonded to other heteroatoms from this group, wherein a number of hydrogen atoms attached to C is optionally replaced by fluorine, wherein the organic residue in each case including all optionally present substituents contains no further heteroatoms from the group consisting of N, S and O as C atoms and is selected from the group consisting of substituted or unsubstituted $C_1$-$C_4$ alkyl, $C_2$-$C_5$ heteroalkyl, $C_3$-$C_6$ cycloalkyl, $C_3$-$C_6$ aryl, $C_2$-$C_6$ heteroaryl, $C_4$-$C_8$ arylalkyl wherein in $NR^1R^2$ the residues $R^1$ and $R^2$ are optionally covalently bonded together with omission of one hydrogen atom in each case, wherein the resultant ring is at most 7-membered, wherein the optionally present substituents of the optionally present residues $R^1$, $R^2$ and $R^3$ are mutually independently selected from the group consisting of:

methyl, ethyl, n-propyl, iso-propyl, n-butyl, iso-butyl, tert.-butyl, cyclopropyl, cyclopentyl, cyclohexyl, cyclooctyl, ethenyl, propenyl, ethynyl, propynyl, trifluoromethyl, methoxy, ethoxy, iso-propoxy, n-butoxy, iso-butoxy, tert.-butoxy, $C_3$ cycloalkoxy, $C_5$ cycloalkoxy, $C_6$ cycloalkoxy, $C_8$ cycloalkoxy, —[—O—$CH_2$—$CH_2$]$_v$-Q or —[—O—$CH_2$—CHMe—]$_v$-Q, wherein Q=OH or is $CH_3$ and wherein v may mean 1 or 2, acetyl, $CO_2$Me, $CO_2$Et, $CO_2$iso-Pr, $CO_2$tert.-Bu, acetyloxy.

Specific embodiment nine comprises (a) The compound of the formula (I) or (b) the mixture comprising one, two or more compounds of the formula (I) or (c) the mixture consisting of two or more compounds of the formula (I) as in any one of the preceding specific embodiments, wherein in case (a) the compound or in case (b) or (c) at least one of the compounds in the mixture is selected from the group consisting of
menthyl oxamate
menthyl N-methyl oxamate
menthyl N,N-dimethyl oxamate
menthyl N-ethyl oxamate
menthyl N,N-diethyl oxamate
menthyl N-propyl oxamate
menthyl N,N-dipropyl oxamate
menthyl N-isopropyl oxamate
menthyl N,N-diisopropyl oxamate
menthyl N-cyclopropyl oxamate
menthyl N-butyl oxamate
morpholin-4yl-oxo-acetic acid (1R,2S,5R)-2-isopropyl-5-methylcyclohexyl ester
menthyl N-(2-methoxyethyl)oxamate
menthyl N-(3-methoxypropanol)oxamate
menthyl N-(2-hydroxyethyl)oxamate
menthyl N-(3-hydroxypropyl)oxamate, Specific embodiment ten comprises (a) The compound of the formula (I) or (b) the mixture comprising one, two or more compounds of the formula (I) or (c) the mixture consisting of two or more compounds of the formula (I) as claimed in any one of the preceding claims, wherein in case (a) the compound or in case (b) or (c) at least one of the compounds in the mixture is selected from the group consisting of
L-menthyl N-methyl oxamate,
D-menthyl N-methyl oxamate,
rac-menthyl N-methyl oxamate,
L-menthyl N-ethyl oxamate,
D-menthyl N-ethyl oxamate,
rac-menthyl N-ethyl oxamate.

Specific embodiment eleven comprises the mixture (b) as in any one of the preceding specific embodiments, consisting of or comprising
(1) one, two or more compounds of the formula (I) and
(2) one or more further substances having a physiological cooling action, wherein the further substance or one; several or all of the further substances (i) cause(s) a taste effect or (ii) cause(s) no taste effect,
and/or
(3) one or more aroma substances without a physiological cooling action
and/or
(4) one or more substances without a physiological cooling action which have a trigeminal or salivatory action.

Specific embodiment twelve comprises the mixture as in specific embodiments eleven, comprising
in constituent (2) one or more further substances with a physiological cooling action without a taste effect
and/or
in constituent (3) one or more aroma substances without a physiological cooling action
and/or
one or more compounds which mutually independently or jointly additionally cause a taste-modulating effect and/or a trigeminal and/or a salivatory-stimulus.

Specific embodiment thirteen comprises a preparation consumed for nutrition or for pleasure or used for oral hygiene or a pharmaceuticals or cosmetic preparation comprising a sufficient amount for achieving a physiological cooling action on the skin and/or mucous membranes of (i) a compound or mixture as claimed in any one of specific embodiments one to ten or (ii) a mixture as in either of specific embodiments eleven or twelve:

Specific embodiment fourteen comprises use of (a) a compound of the formula (I) or (b) a mixture comprising one, two or more compounds of the formula (I) or (c) a mixture consisting of two or more compounds of the formula (I)

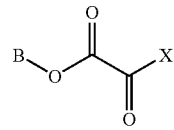

wherein the following in each case applies:
B means a hydrocarbon residue selected from the following group:

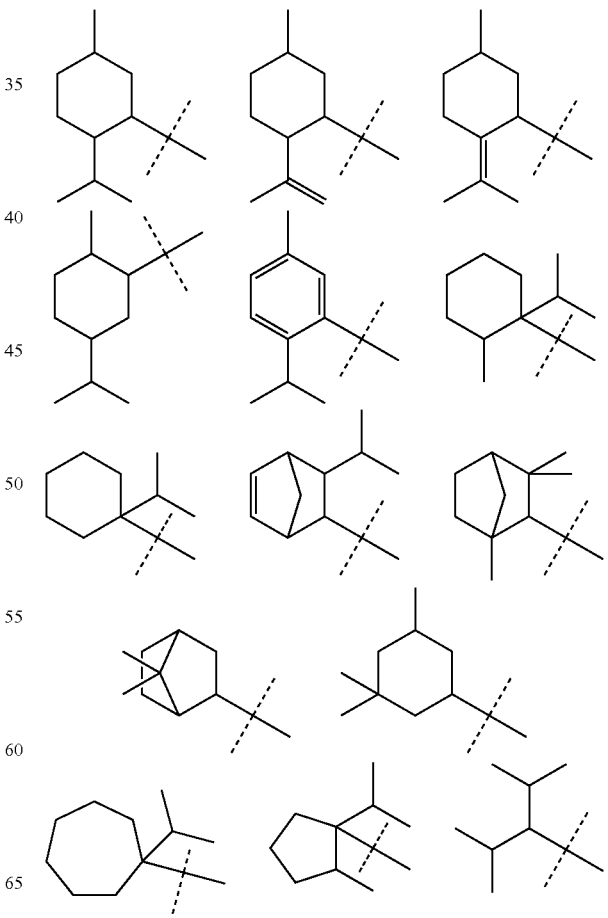

-continued

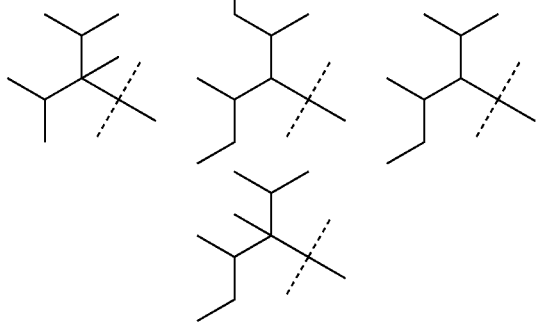

in which the dashed line indicates the bond which links the hydrocarbon residue B with the adjacent oxygen atom in formula (I), X means $NR^1R^2$ or $SR^3$, wherein in each case mutually independently in $NR^1R^2$ the residues $R^1$ and $R^2$ are selected and in $SR^3$ the residue $R^3$ is selected from the group consisting of:

hydrogen and organic residue with 1 to 12 C atoms which is selected from the group consisting of substituted or unsubstituted alkyl, heteroalkyl, cycloalkyl, heterocycloalkyl, cycloalkylalkyl, alkenyl, cycloalkenyl, cycloalkenylalkyl, alkynyl, cycloalkylalkynyl, aryl, heteroaryl, arylalkyl, cycloalkylaryl, cycloalkenylaryl, cycloalkylheteroaryl, heterocycloalkylaryl, heterocycloalkenylaryl, heterocycloalkenylheteroaryl and heteroarylalkyl, wherein optionally in $NR^1R^2$ the residues $R^1$ and $R^2$ are covalently bonded together with omission of one hydrogen atom in each case and with formation of a ring (i) for producing a cooling action on the skin or a mucous membrane for other than therapeutic purposes or (ii) for producing a medicament.

Specific embodiment fifteen comprises the use as in specific embodiment fourteen for producing a medicament, wherein the medicament to be produced serves to combat or alleviate coughs, colds, symptoms of oral, nasal, throat or pharyngeal inflammation, sore throat or hoarseness.

Specific embodiment sixteen comprises a therapeutic or non-therapeutic method for achieving a physiological cooling action on the skin and/or a mucous membrane comprising the following step:

applying an amount sufficient to achieve a physiological cooling action (1) of a compound or a mixture as in any one of the preceding specific embodiments one to ten or (2) of a mixture as in either of specific embodiment eleven or specific embodiment twelve or (3) of a preparation as in specific embodiment thirteen onto the skin and/or a mucous membrane.

Specific embodiment seventeen comprises a method for the production of the compound as claimed in any one of specific embodiments one to ten comprising the steps:

(1) providing a mixed oxalic acid ester of the formula

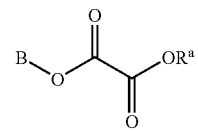

wherein $R^a$ means an alkyl residue, preferably a $C_1$-$C_4$ alkyl residue, or oxalic acid halide of the formula

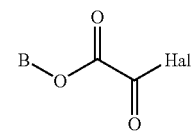

wherein Hal means halide, (2) providing an amine $HNR^1R^2$ or thiol $HSR^3$ or a corresponding salt, (3) reacting the provided compounds with one another, such that a compound as recited in any one of specific embodiments one to ten is obtained.

What is claimed is:

1. A composition comprising one or more compounds of formula (I)

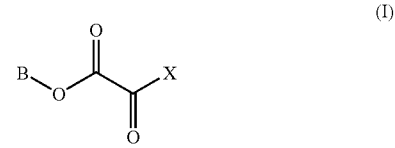

wherein:

B is a hydrocarbon residue selected from the group consisting of:

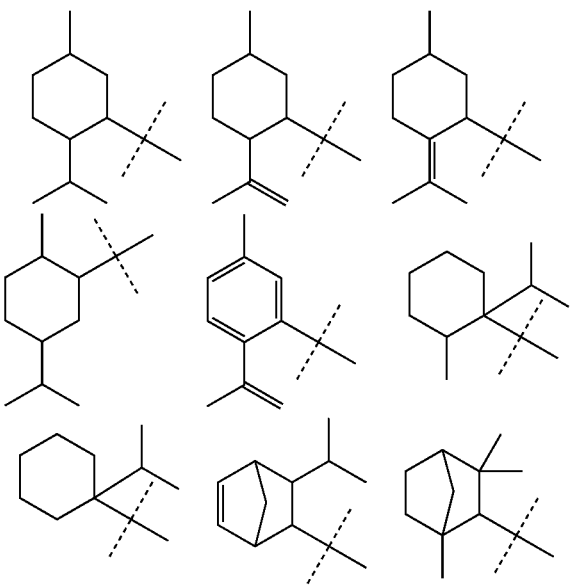

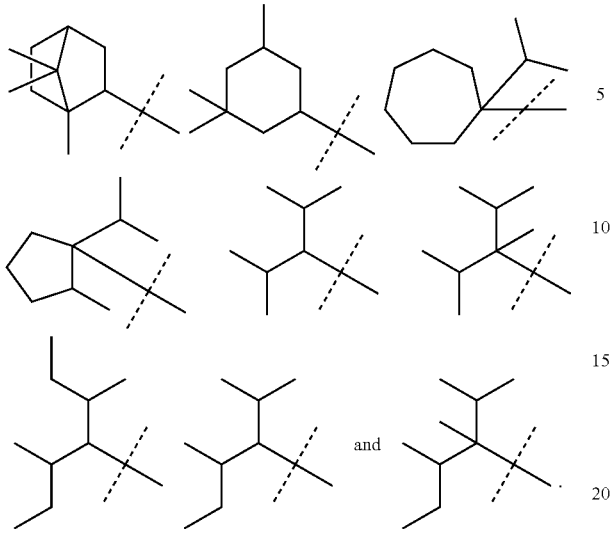

in which the dashed line indicates a bond which links the hydrocarbon residue B with the adjacent oxygen atom in formula (I), X is $NR^1R^2$ or $SR^3$, and $R^1$, $R^2$, and $R^3$ are independently selected from the group consisting of hydrogen and an optionally substituted organic residue with 1 to 12 C atoms, wherein, optionally in $NR^1R^2$, the residues $R^1$ and $R^2$ are covalently bonded together with omission of one hydrogen atom in each case to form a ring;

provided that when the composition comprises only one compound of formula (I), the one compound is not selected from the group consisting of

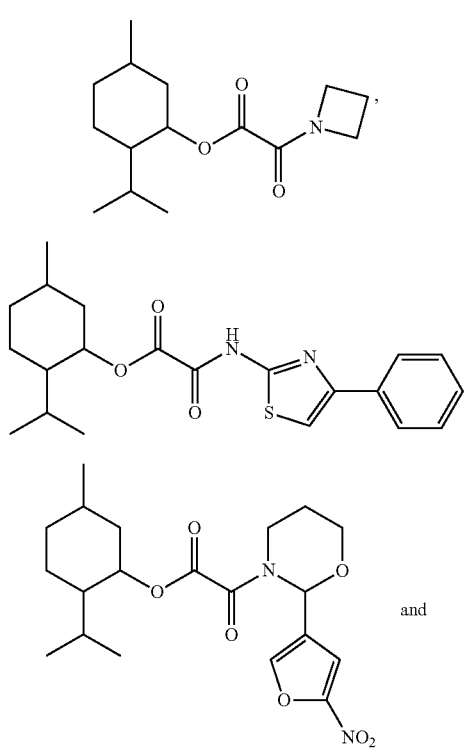

wherein at least one compound of formula (I) is selected from the group consisting of:
(L)-menthyl oxamate,
rac-menthyl oxamate,
menthyl N-methyl oxamate,
menthyl N,N-dimethyl oxamate,
menthyl N-ethyl oxamate,
menthyl N,N-diethyl oxamate,
menthyl N-propyl oxamate,
menthyl N,N-dipropyl oxamate,
menthyl N-isopropyl oxamate,
menthyl N,N-diisopropyl oxamate,
menthyl N-cyclopropyl oxamate,
menthyl N-butyl oxamate,
morpholin-4-yl-oxo-acetic acid (1R,2S,5R)-2-isopropyl-5-methylcyclohexyl ester,
menthyl N-(2-methoxyethyl) oxamate,
menthyl N-(3-methoxypropanol) oxamate,
menthyl N-(2-hydroxyethyl) oxamate, and
menthyl N-(3-hydroxypropyl) oxamate.

2. The composition according to claim 1, wherein the organic residue is selected from the group consisting of substituted or unsubstituted: $C_1$-$C_{10}$ alkyl, $C_1$-$C_{10}$ heteroalkyl, $C_2$-$C_{10}$ heterocycloalkyl, $C_3$-$C_{10}$ cycloalkyl, $C_4$-$C_{10}$ cycloalkylalkyl, $C_2$-$C_{10}$ alkenyl, $C_3$-$C_{10}$ cycloalkenyl, $C_4$-$C_{10}$ cycloalkenylalkyl, $C_2$-$C_{10}$ alkynyl, $C_5$-$C_{10}$ cycloalkylalkynyl, $C_3$-$C_{10}$ aryl, $C_2$-$C_{10}$ heteroaryl, $C_4$-$C_{10}$ arylalkyl, $C_8$-$C_{10}$ cycloalkylaryl, $C_8$-$C_{10}$ cycloalkenylaryl, $C_5$-$C_{10}$ cycloalkylheteroaryl, $C_8$-$C_{10}$ heterocycloalkylaryl, $C_8$-$C_{10}$ heterocycloalkenylaryl, $C_8$-$C_{10}$ heterocycloalkenylheteroaryl and $C_3$-$C_{10}$ heteroarylalkyl;

wherein a number of hydrogen atoms attached to C is optionally replaced by fluorine, and the organic residue has no more than 3 heteroatoms independently selected from the group consisting of N, S, and O, wherein O and S are not bonded to another heteroatom.

3. The composition according to claim 1, wherein in at least one compound of formula (I), X is $NHR^1$.

4. The composition according to claim 1, wherein in at least one compound of formula (I), B is a hydrocarbon residue selected from the group consisting of:

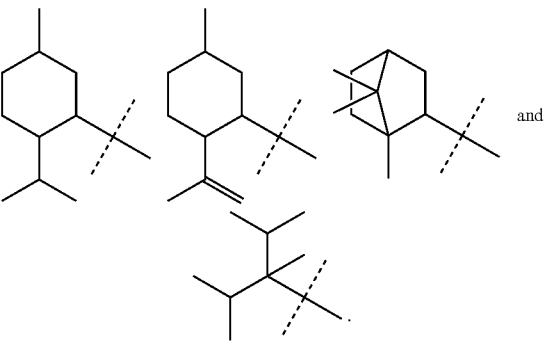

5. The composition of claim 1, wherein in at least one compound of formula (I), B is L-menthyl, D-menthyl or rac-menthyl.

6. The composition according to claim 1, wherein in at least one compound of formula (I), the optional substitutents on the organic residue are independently selected from the group consisting of $C_1$-$C_5$ alkyl, $C_3$-$C_8$ cycloalkyl, $C_2$-$C_4$ alkenyl, $C_2$-$C_4$ alkynyl, propynyl, $C_1$-$C_4$ perfluoroalkyl, hydroxy, $C_1$-$C_8$ alkoxy, $C_3$-$C_8$ cycloalkoxy, $C_1$-$C_4$ acyl, $C_1$-$C_4$ alkoxycarbonyl, $C_1$-$C_4$ acyloxy and $C_2$-$C_7$ heteroalkyl.

7. The composition according to claim 1, wherein in at least one compound of formula (I), when X is $NR^1R^2$, and $R^1$ and $R^2$ are covalently bonded together with omission of one hydrogen atom in each case to form, at most, a 7 membered ring.

8. The composition according to claim 5, wherein in at least one compound of formula (I), X is $NR^1R^2$, and the organic residue is selected from the group consisting of substituted or unsubstituted: $C_1$-$C_4$ alkyl, $C_2$-$C_5$ heteroalkyl, $C_3$-$C_6$ cycloalkyl, $C_3$-$C_6$ aryl, $C_2$-$C_6$ heteroaryl, and $C_4$-$C_8$ arylalkyl,
wherein if $R^1$ and $R^2$ are covalently bonded together to form a ring, the ring is at most 7-membered, and
wherein the optionally present substituents of the organic residue are selected from the group consisting of: methyl, ethyl, n-propyl, iso-propyl, n-butyl, iso-butyl, tert-butyl, cyclopropyl, cyclopentyl, cyclohexyl, cyclooctyl, ethenyl, propenyl, ethynyl, propynyl, trifluoromethyl, methoxy, ethoxy, iso-propoxy, n-butoxy, iso-butoxy, tert-butoxy, $C_3$ cycloalkoxy, $C_5$ cycloalkoxy, $C_6$ cycloalkoxy, $C_8$ cycloalkoxy, —[—O—$CH_2$—$CH_2$—]$_v$-Q or —[—O—$CH_2$—CHMe-]$_v$-Q, wherein Q=OH or is $CH_3$ and wherein v may mean 1 or 2, acetyl, $CO_2$Me, $CO_2$Et, $CO_2$iso-Pr, $CO_2$tert-Bu, and acetyloxy.

9. The composition of claim 1, wherein at least one compound of formula (I) is selected from the group consisting of:
L-menthyl N-methyl oxamate,
D-menthyl N-methyl oxamate,
rac-menthyl N-methyl oxamate,
L-menthyl N-ethyl oxamate,
D-menthyl N-ethyl oxamate, and
rac-menthyl N-ethyl oxamate.

10. The composition according to claim 1 comprising:
(1) one or more compounds of the formula (I) and
(2) one or more physiological cooling active ingredients, wherein the one or more physiological cooling active ingredients bring about a sensation of coolness on the skin or mucous membranes without any physical cooling or evaporation occurring
and/or
(3) one or more aroma substances without a physiological cooling action
and/or
(4) one or more substances without a physiological cooling action which have a trigeminal or salivatory action.

11. The composition as claimed in claim 10, wherein
constituent (2) comprises one or more further substances with a physiological cooling action without a taste effect
and/or
constituent (3) comprises one or more aroma substances without a physiological cooling action
and/or,
the composition further comprises one or more compounds which mutually independently or jointly additionally cause a taste-modulating effect and/or a trigeminal and/or a salivatory stimulus.

12. A preparation for nutrition or for pleasure or used for oral hygiene or a pharmaceutical or cosmetic preparation comprising a composition of claim 1, wherein the compound or compounds of formula (I) is/are present in an amount of 0.0001 wt. % to 20 wt. % of the preparation, and an auxiliary substance and/or additive which is/are present in an amount of 0.0000001 wt. % to 99.99 wt. % of the preparation.

13. A pharmaceutical preparation comprising a composition of claim 1, wherein the pharmaceutical preparation is in the form of a capsule, a tablet, a sugar-coated tablet, a granule, a pellet, a mixture of solids, a dispersion in a liquid phase, an emulsion, a powder, a solution, or a paste.

14. The pharmaceutical preparation as claimed in claim 13, wherein the pharmaceutical preparation is a tablet coated by a coating that is resistant to gastric juices.

15. A method for achieving a physiological cooling action on skin and/or a mucous membrane comprising applying onto the skin and/or the mucous membrane an amount of a composition as claimed in claim 1 sufficient to achieve a physiological cooling action.

16. The composition of claim 2, wherein the organic residue is independently selected from the group consisting of substituted or unsubstituted $C_1$-$C_8$ alkyl, $C_2$-$C_8$ heteroalkyl, $C_1$-$C_8$ heterocycloalkyl, $C_3$-$C_8$ cycloalkyl, $C_4$-$C_8$ cycloalkylalkyl, $C_2$-$C_8$ alkenyl, $C_3$-$C_8$ cycloalkenyl, $C_4$-$C_8$ cycloalkenylalkyl, $C_3$-$C_6$ aryl, $C_2$-$C_6$ heteroaryl, and $C_4$-$C_8$ arylalkyl.

17. The composition of claim 6, wherein the optional substituents are independently selected from the group consisting of methyl, ethyl, n-propyl, iso-propyl, n-butyl, iso-butyl, tert-butyl, cyclopropyl, cyclopentyl, cyclohexyl, cyclooctyl, ethenyl, propenyl, ethynyl, propynyl, trifluoromethyl, methoxy, ethoxy, iso-propoxy, n-butoxy, iso-butoxy, tert-butoxy, $C_3$ cycloalkoxy, $C_5$ cycloalkoxy, $C_6$ cycloalkoxy, $C_8$ cycloalkoxy, —[—O—$CH_2$—$CH_2$—]$_v$-Q or —[—O—$CH_2$—CHMe-]$_v$-Q, wherein Q=OH or is $CH_3$ and wherein v may mean 1 or 2, acetyl, $CO_2$Me, $CO_2$Et, $CO_2$iso-Pr, $CO_2$tert-Bu, and acetyloxy.

18. The composition of claim 1, wherein X is $NR^1R^2$ and $NR^1R^2$ is selected from the group consisting of piperidinyl and morpholinyl.

19. A preparation for nutrition, pleasure, or oral hygiene, or a pharmaceutical or cosmetic preparation, comprising a sufficient amount of a composition as claimed in claim 6 for achieving a physiological cooling action on skin and/or mucous membranes, and further comprising:
(1) one or more physiological cooling active ingredients, wherein the one or more physiological cooling active ingredients bring about a sensation of coolness on the skin or mucous membranes without any physical cooling or evaporation occurring,
and/or
(2) one or more aroma substances without a physiological cooling action
and/or
(3) one or more substances without a physiological cooling action which have a trigeminal or salivatory action.

20. The composition of claim 10, wherein the composition, comprises 0.0001 wt. % to 20 wt. % of a compound or compounds according to formula (I) and 0.0000001 wt. % to 99.99 wt. % of an auxiliary substance and/or additive, relative to the total weight of the composition.

21. A method for achieving a physiological cooling action on skin and/or a mucous membrane comprising applying a sufficient amount of a composition of claim 6 onto the skin and/or the mucous membrane to achieve a physiological cooling action.

22. A method for achieving a physiological cooling action on skin and/or a mucous membrane comprising applying a sufficient amount of a composition of claim 10 onto the skin and/or mucous membrane to achieve a physiological cooling action.

23. A method for achieving a physiological cooling action on skin and/or a mucous membrane comprising applying a sufficient amount of a composition of claim 12 onto the skin/or mucous membrane to achieve a physiological cooling action.

24. A method for producing a compound of formula (I) as defined in claim 1, comprising reacting an oxalic acid ester of the formula

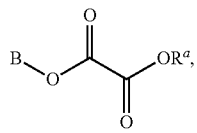

wherein $R^a$ is an alkyl residue, or oxalic acid halide of the formula

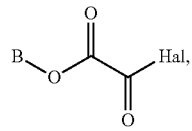

wherein Hal is a halide, with
an amine $HNR^1R^2$ or thiol $HSR^3$, or a corresponding salt.

25. The method of claim 24, wherein $R^a$ is a $C_1$-$C_4$ alkyl residue.

* * * * *

UNITED STATES PATENT AND TRADEMARK OFFICE
CERTIFICATE OF CORRECTION

PATENT NO. : 8,344,025 B2  
APPLICATION NO. : 12/193375  
DATED : January 1, 2013  
INVENTOR(S) : Horst Surburg et al.

Page 1 of 1

It is certified that error appears in the above-identified patent and that said Letters Patent is hereby corrected as shown below:

In the Claims:

At column 47, claim number 1, line number 20, the "." should be changed to a --,--

At column 51, claim number 24, line numbers 6-7, should read as follows:

A method for producing ~~a compound of formula (I) as defined in claim 1~~ <u>a composition of claim 1</u>, comprising reacting an oxalic acid ester of Signed and Sealed this  
Fourteenth Day of May, 2013

Teresa Stanek Rea  
*Acting Director of the United States Patent and Trademark Office*